(12) United States Patent
Anderson et al.

(10) Patent No.: US 8,409,818 B2
(45) Date of Patent: Apr. 2, 2013

(54) METHOD OF DIAGNOSIS AND KIT THEREFOR

(75) Inventors: David Andrew Anderson, Brunswick (AU); Robyn Elizabeth Lloyd, New Farm (AU); Suzanne Mary Crowe, Melbourne (AU); Mary Louise Garcia, North Fitzroy (AU); Alan Lee Landay, River Forest, IL (US)

(73) Assignee: The Macfarlane Burnet Institute for Medical Research and Public Health Limited, Melbourne, Victoria (AU)

( * ) Notice: Subject to any disclaimer, the term of this patent is extended or adjusted under 35 U.S.C. 154(b) by 749 days.

(21) Appl. No.: 12/443,306

(22) PCT Filed: Sep. 28, 2007

(86) PCT No.: PCT/AU2007/001449
§ 371 (c)(1),
(2), (4) Date: Jul. 21, 2009

(87) PCT Pub. No.: WO2008/037026
PCT Pub. Date: Apr. 3, 2008

(65) Prior Publication Data
US 2011/0244480 A1 Oct. 6, 2011

(30) Foreign Application Priority Data
Sep. 28, 2006 (AU) .................................. 2006905393

(51) Int. Cl.
*G01N 33/00* (2006.01)
*G01N 1/00* (2006.01)

(52) U.S. Cl. .................... 435/7.24; 435/7.23; 435/7.92; 435/40.51; 435/287.9; 435/288.4; 436/518; 436/538; 436/540; 436/548; 436/10; 436/63; 436/64; 436/161; 436/166; 436/175; 436/177

(58) Field of Classification Search .................... 435/7.2, 435/7.23–7.25, 7.92, 7.94, 40.51, 287.2, 435/287.9, 288.6, 288.4; 436/518, 523, 524, 436/526, 528, 538, 540, 546, 548, 10, 46, 436/63, 64, 161, 165, 166, 171, 172, 175, 436/177
See application file for complete search history.

(56) References Cited

U.S. PATENT DOCUMENTS
5,292,636 A   3/1994   Kung et al.
5,811,525 A   9/1998   Rittershaus
(Continued)

FOREIGN PATENT DOCUMENTS
WO        93/23559        11/1993
WO    2006/098724 A1      9/2006
WO    WO 2006/098724  *   9/2006

OTHER PUBLICATIONS
Johnson et al. Evaluation of Four Alternative Methodologies for Determination of Absolute CD4+ Lymphocyte Counts, Journal of Acquired Immune Deficiency Syndromes and Human Retrovirology, 10: 522-530 (1995).*
(Continued)

*Primary Examiner* — Gail R Gabel
(74) *Attorney, Agent, or Firm* — Scully, Scott, Murphy & Presser, P.C.

(57) ABSTRACT

The invention provides kits and methods for detecting or monitoring the number of cells in sample. The cell comprises a cell surface associated protein (CSAP) comprising a cytoplasmic (cytosolic) and an extracellular (ecto) domain. The kit comprises: (i) a chromatographic device; and (ii) a CSAP-binding agent. The method comprises: (i) optionally contacting the sample with an agent capable of lysing or permeabilizing CSAP bearing cells; (ii) contacting the sample with a CSAP-binding agent that binds to the cytoplasmic domain of the CSAP; and (iii) directly or indirectly evaluating the level or presence of bound CSAP in the sample.

12 Claims, 32 Drawing Sheets

---

Two peptides based on human CD4cyto were synthesised:

– Peptide 1 (17 amino acids):
 • H-KRLLSEKKTCPHRFQKT-NH2
 ($_{446}QC_{447}$ & $_{455}CSPI_{458}$ omitted*)

– Peptide 2 (20 amino acids):
 • H-CRHRRRQAERMSQIKRLLSE-NH2
 ($_{421}R_{421}$ omitted*)

```
                                    Peptide 1
human CD4cyto:  ₄₂₁rcrhrrrqae rmsqikrlls ekktcqcphr fqktcspi₄₅₈
                              Peptide 2
```

U.S. PATENT DOCUMENTS

| | | | |
|---|---|---|---|
| 6,136,549 | A | 10/2000 | Feistel |
| 7,157,049 | B2 * | 1/2007 | Valencia et al. ............. 422/68.1 |
| 2005/0202521 | A1 | 9/2005 | Crum |
| 2006/0240569 | A1 | 10/2006 | Goldenbaum et al. |

OTHER PUBLICATIONS

Paxton H. et al., "Comparison of CD4 Cell Count by a Simple Enzyme-Linked Immunosorbent Assay Using the TRAx CD4 Test Kit and by Flow Cytometry and Hematology", *Clinical and Diagnostic Laboratory Immunology* 2(1): 104-114 (1995).

Carella A. V. et al., "A Manual Bead Assay for the Determination of Absolute CD44+ and CD8+ Lymphocyte Counts in Human Immunodeficiency Virus-Infected Individuals", *Clinical and Diagnostic Laboratory Immunology* 2(5): 623-625 (1995).

Johnson D. et al., "Evaluation of Four Alternative Methodologies for Determination of Absolute CD4+ Lymphocyte Counts", *Journal of Acquired Immune Deficiency Syndromes and Human Retrovirology* 10:522-530 (1995).

International Search Report, dated Dec. 10, 2007 issued in respect to corresponding International Patent Application No. PCT/AU2007/001449.

"Anti-CD4, Intracellular, Clone 024-10D6.B3" *Millipore On-line Catalogue* XP002593025, Retrieved from the Internet: URL: hhtp://www.millipore.com/catalogue/item/MAB3706, retrieved on Jul. 21, 2010.

Supplementary European Search Report dated Jul. 22, 2010 issued in respect to corresponding European Application No. EP 07 81 5265.

* cited by examiner

Two peptides based on human CD4cyto were synthesised:

— Peptide 1 (17 amino acids):
- H-KRLLSEKKTCPHRFQKT-NH2

($_{446}$QC$_{447}$ & $_{455}$CSPI$_{458}$ omitted*)

— Peptide 2 (20 amino acids):
- H-CRHRRRQAERMSQIKRLLSE-NH2

($_{421}$R$_{421}$ omitted*)

human CD4cyto: $_{421}$rcrhrrrqae rmsqikrlls ekktcqephr fqktcspi$_{458}$

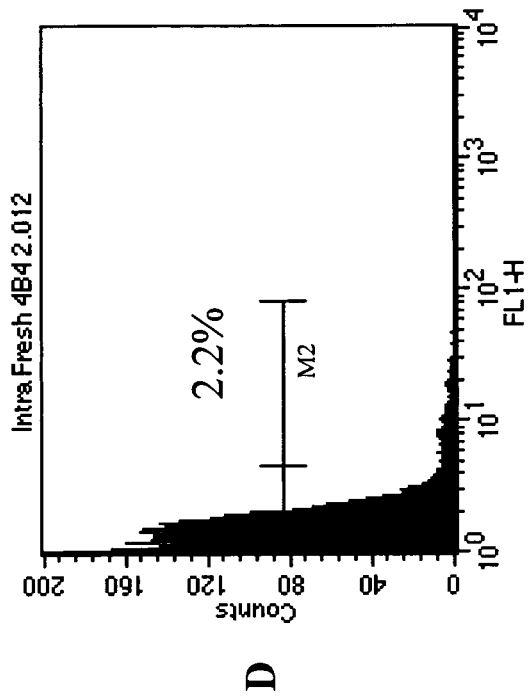
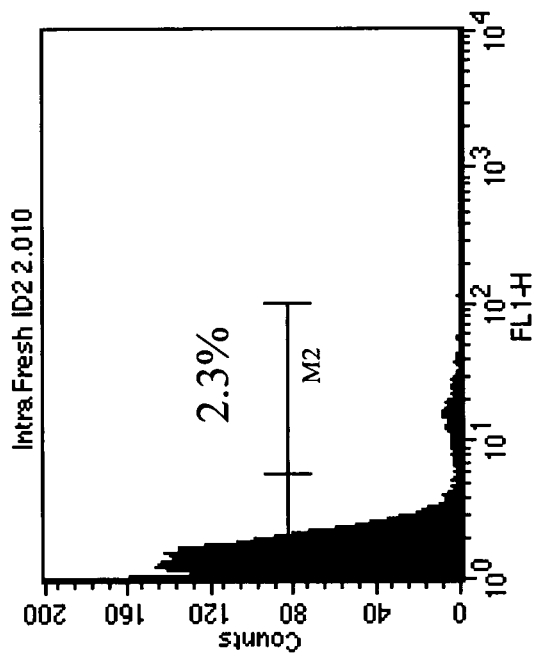
Figure 6 continued

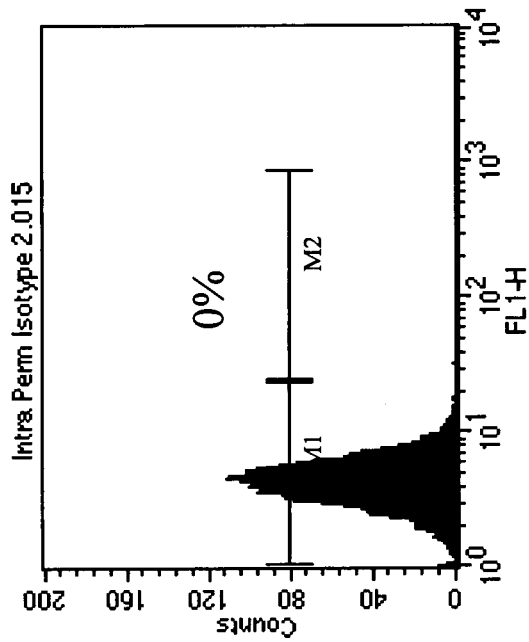
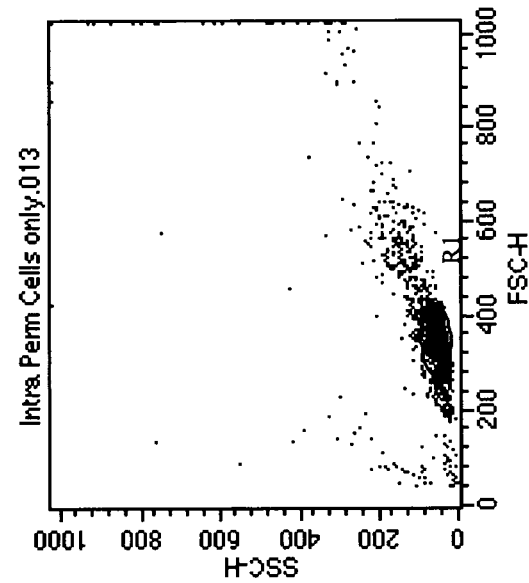
Figure 7

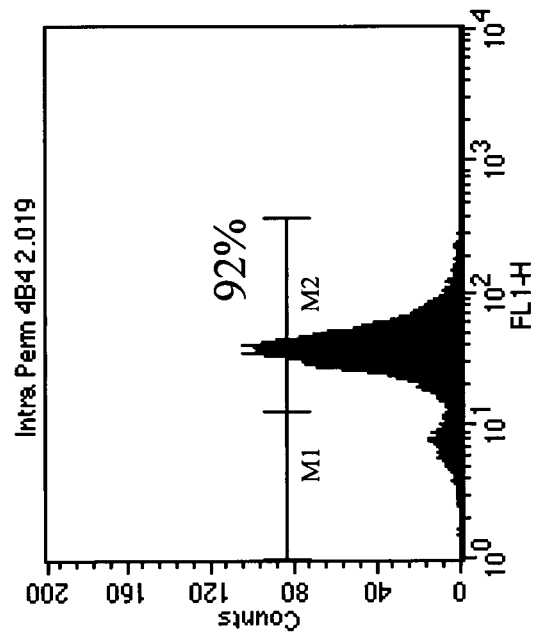
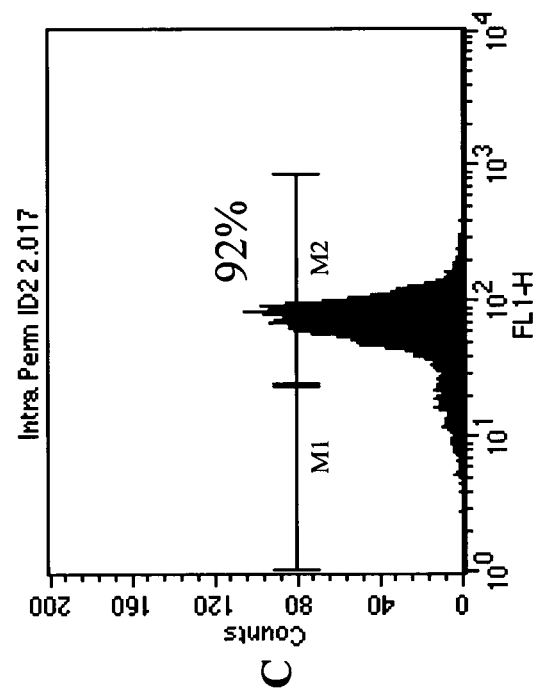
Figure 7 continued

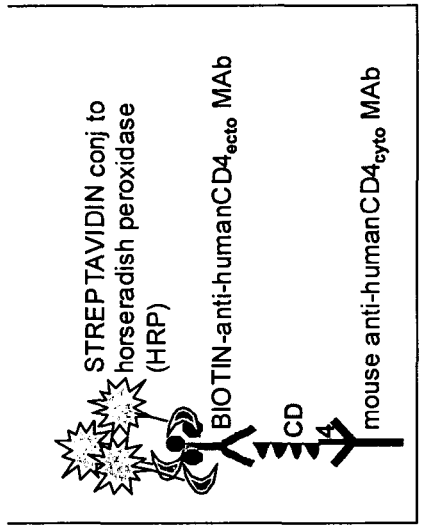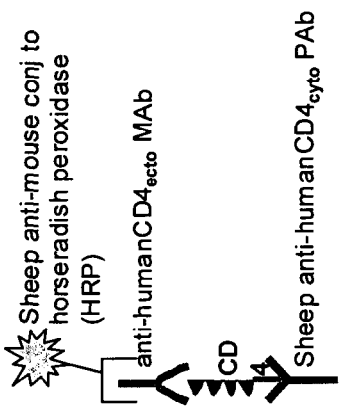
Figure 8

TM^CD4 nucleotide sequence

```
atg ggg ggt tct CAT CAT CAT CAT CAT CAT ggt atg gct agc
atg act ggt GAT AAG gga cag caa atg ggt cgg GAT CTG TAC GAC GAT ATG
GAC GAT CGG gta cca tcc agt gtg gtg gaa ttc aca CTG CAA
AAC CGG GGA GTC CCT TTT GCA ACT CAG AAA GTG CTT GTG GTG
CTG GCG CTC CCA GCA GAT GTG GGA AAG GTG AAA GCT
CTG GGC AAA AAG GGG ACA CAA TTC CAC ACC TGT ACA GCT
TCC CAG ATA AAG CTG GGA AAT GAT TTC CAG AAC TCC AAA
CAG ATA AAG TCC AAG ATT CTG GGA AAT GAT TTT CAG GGC TTT ACT AAA
GGT CCA TCC GAC CAA CTG TCA GAT CGC CCC CTG ATC AGA AGA AGC
CTT TGG GAC GAA GAC TCA GTG CAC TTG CCC CTG ATC AAG AAT CTT
AAG ATA GAA GAG GAG ACC CAC CCC AGT AGC GGG GAC ACG GAG GAC
CAG AAG GAG GAG ACC CAC CCC GGT AGC AGC CCC CTG CAG ACC CTG
ACC TTG GAG AGC CCT CTT AAA AAC CTC CAG AAG GTG ACC TGT
AGG AGT CCA AGG GGT AAA GAG CTC TTC CAG GAG AGG TTC CAA ACC CTC
TCC GTG TCT CAG TTG CAG AAC CAG AAG GTG GGC ACC TGG ACA
TGC ACT GTC GTG CTA GCT TTC CAG GTG GAG TTC AGC ATA
GAC ATC GTG AAA AAG GGG GAA AAG GTG GAG TTC TCC ATA GTC
TAT AAG GAG GTG AAA AAG GGA GAA CAG CTG GAG TTC TCC CCA CTC
GCC TTT ACA GTT GAA AAG CTG ACG GGC AGT GGC GAG CTG TGG
```

Figure 16

TGG CAG GCG GAG AGG GCT TCC TCC TCC AAG TCT TGG ATC ACC
TTT GAC CTG AAG AAC AAG GAA GTG TCT GTA AAA CGG GTT ACC
CAG GAC CCT AAG CTC CAG ATG GGC AAG AAG CTC CCG CTC CAC
CTC ACC CTG CCC CAG GCC TTG CCT CAG TAT GCT GGC TCT
GGA AAC CTC ACC CTG GCC CTT GAA GCG AAA ACA GGA AAG TTG
CAT CAG GAA GTG AAC CTG GTG GTG ATG AGA GCC ACT CAG CTC
CAG AAA AAT TTG ACC TGT GAG GTG TGG GGA CCC ACC TCC CCT
AAG CTG ATG CTG AGT TTG AAA CTG GAG AAC AAG GAG GCA AAG
GTC TCG AAG CGG GAG AAG GCG GTG TGG GTG CTG AAC CCT GAG
GCG GGG ATG TGG CAG TGT CTG CTG AGT GAC TCG GGA CAG GTC
CTG CTG GAA TCC AAC ATC AAG GTT CTG CCC ACA TGG TCC ACC
CCG GTG CAG *AGG TGC CGG CAC CGA AGG CGC CAA GCA GAG CGG*
*ATG TCT CAG ATC AAG AGA CTC CTC AGT GAG AAG AAG ACC TGC*
*CAG TGT CCT CAC CGG TTT CAG AAG ACA TGT AGC CCC ATT TGA*

Figure 16 continued

TM^CD4 amino acid sequence

Met Gly Gly Ser His His His His His His Gly Met Ala Ser
Met Thr Gly Gly Gln Gln Met Gly Arg Asp Leu Tyr Asp Asp
Asp Asp Lys Val Pro Gly Ser Ser Val Val Glu Phe Thr Met
Asn Arg Gly Val Pro Phe Arg His Leu Leu Leu Val Leu Gln
Leu Ala Leu Leu Pro Ala Ala Thr Gln Gly Lys Lys Val Val
Leu Gly Lys Lys Gly Asp Thr Val Glu Leu Thr Cys Thr Ala
Ser Gln Lys Lys Ser Ile Gln Phe His Trp Lys Asn Ser Asn
Gln Ile Lys Ile Leu Gly Asn Gln Gly Ser Phe Leu Thr Lys
Gly Pro Ser Lys Leu Asn Asp Arg Ala Asp Ser Arg Arg Ser
Leu Trp Asp Gln Gly Asn Phe Pro Leu Ile Ile Lys Asn Leu
Lys Ile Glu Asp Ser Asp Thr Tyr Ile Cys Glu Val Glu Asp
Gln Lys Glu Glu Val Gln Leu Leu Val Phe Gly Leu Thr Ala
Asn Ser Asp Thr His Leu Leu Gln Gly Gln Ser Leu Thr Leu
Thr Leu Glu Ser Pro Pro Gly Ser Ser Pro Ser Val Gln Cys
Arg Ser Pro Arg Gly Lys Asn Ile Gln Gly Gly Lys Thr Leu
Ser Val Ser Gln Leu Glu Leu Gln Asp Ser Gly Thr Trp Thr
Cys Thr Val Leu Gln Asn Gln Lys Lys Val Glu Phe Lys Ile
Asp Ile Val Val Leu Ala Phe Gln Lys Ala Ser Ser Ile Val
Tyr Lys Lys Glu Gly Glu Gln Val Glu Phe Ser Phe Pro Leu
Ala Phe Thr Val Glu Lys Leu Thr Gly Ser Gly Glu Leu Trp

Figure 17

| Trp | Gln | Ala | Glu | Arg | Ala | Ser | Ser | Ser | Lys | Ser | Trp | Ile | Thr |
| --- | --- | --- | --- | --- | --- | --- | --- | --- | --- | --- | --- | --- | --- |
| Phe | Asp | Leu | Lys | Asn | Lys | Glu | Val | Ser | Val | Lys | Arg | Val | Thr |
| Gln | Asp | Pro | Lys | Leu | Gln | Met | Gly | Lys | Lys | Leu | Pro | Leu | His |
| Leu | Thr | Leu | Pro | Gln | Ala | Leu | Pro | Gln | Tyr | Ala | Gly | Ser | Gly |
| Asn | Leu | Thr | Leu | Ala | Leu | Glu | Ala | Lys | Thr | Gly | Lys | Leu | His |
| Gln | Glu | Val | Asn | Leu | Val | Val | Met | Arg | Ala | Thr | Gln | Leu | Gln |
| Lys | Asn | Leu | Thr | Cys | Glu | Val | Trp | Gly | Pro | Thr | Ser | Pro | Lys |
| Leu | Met | Leu | Ser | Leu | Lys | Leu | Glu | Asn | Lys | Glu | Ala | Lys | Val |
| Ser | Lys | Arg | Glu | Lys | Ala | Val | Trp | Val | Leu | Asn | Pro | Glu | Ala |
| Gly | Met | Trp | Gln | Cys | Leu | Leu | Ser | Asp | Ser | Gly | Gln | Val | Leu |
| Leu | Glu | Ser | Asn | Ile | Lys | Val | Leu | Pro | Thr | Trp | Ser | Thr | Pro |
| Val | Gln | Arg | His | Arg | Arg | Gln | Ala | Gln | Ala | Glu | Met | Ser | Gln |
| *Ile* | *Lys* | *Leu* | *Leu* | *Ser* | *Glu* | *Lys* | *Lys* | *Thr* | *Cys* | *Gln* | *Arg* | *Met* | *Gln* |
| *His* | *Arg* | *Phe* | *Gln* | *Lys* | *Thr* | *Cys* | *Ser* | *Pro* | *Ile* | \* | \* | \* | |

Figure 17 continued

A.
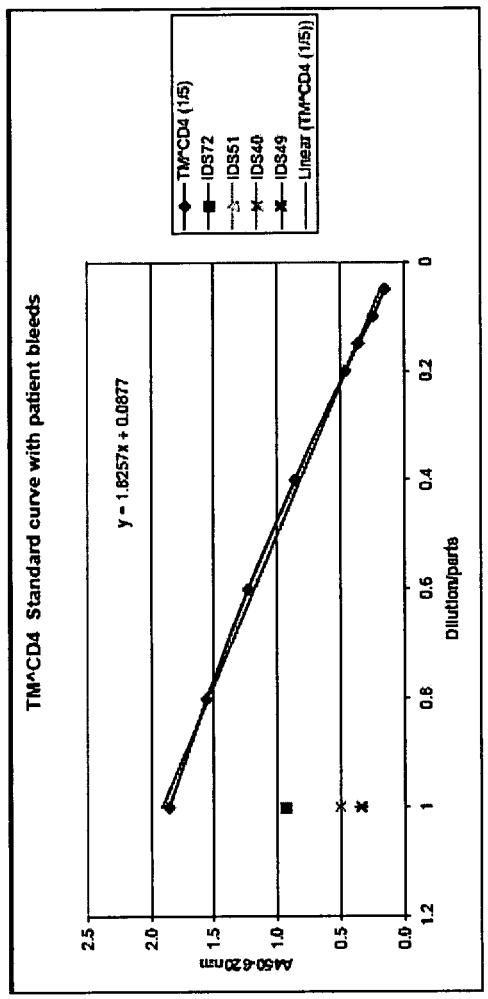
B.
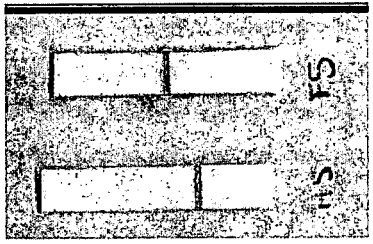
Figure 19

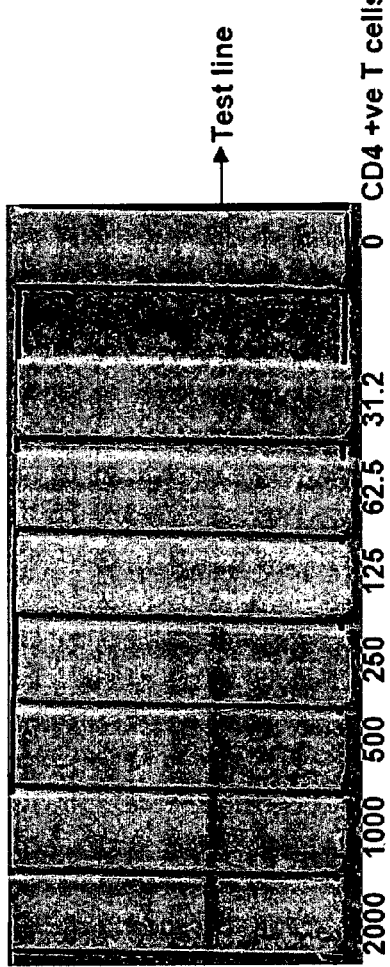 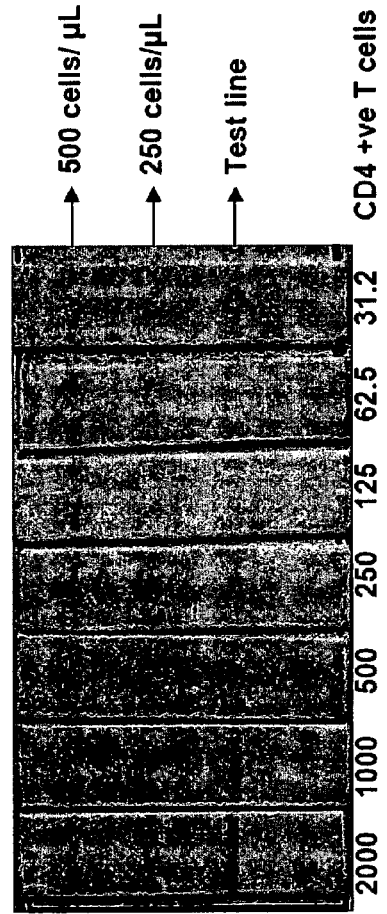
Figure 22

METHOD OF DIAGNOSIS AND KIT THEREFOR

FIELD

The present invention relates generally to the field of diagnosis and provides methods and reagents for accurately assessing in a sample from a subject the presence or amount of a specific cell type, its cell-associated proteins or soluble (extracellular) forms thereof. In some embodiments, the invention relates to rapid, self contained diagnostics which can be used in most environments such as the clinic, laboratory, in the field, at home and in regions having poor resources. In one embodiment, a method and kit is provided for evaluating CD4 T-cell numbers in a sample from a subject.

BACKGROUND

Bibliographic details of references in the subject specification are also listed at the end of the specification.

Reference to any prior art in this specification is not, and should not be taken as, an acknowledgement or any form of suggestion that this prior art forms part of the common general knowledge in any country.

A diverse range of techniques are used in research, analysis, development and clinically to detect cells of interest. Manual or automated techniques are available to count cells in specially designed chambers that permit cell numbers in a sample to be evaluated. Cells may be stained with particular stains in order to differentiate between cell types. Histochemical techniques may be applied to further differentiate between cells in a sample. The ability of cells to respond to particular antigens by proliferating or producing cytokines, bind other cells, engulf other cells or move by chemotaxis may also be diagnostic. Cell surface markers are particularly useful for differentiating between cell types and evaluating the number of particular cells in a sample. Many techniques use antibodies to detect the presence of the marker.

Cells of prokaryotic and eukaryotic organisms, in all their different forms, comprise a cell membrane, which separates the contents of the cell from the extracellular environment. The cell membrane is a selective barrier that determines what goes in and out of the cell and which also undertakes complex signalling activities with other cells and molecules in the environment of the cell. The membrane comprises a phospholipid bilayer and most molecules that cross or interact with the bilayer do so with the assistance of proteins inserted into the bilayer that have both cytoplasmic and extracellular portions.

Frequently, a cell's initial interaction with its surroundings occurs via receptors or cell surface associated molecules expressed on the plasma membrane. Activation of these receptors, whether through binding endogenous ligands (such as cytokines or hormones) or exogenous ligands (such as antigens) triggers a biochemical cascade from the membrane through the cytoplasm to the nucleus. A wide range of receptors or cell surface associated proteinaceous molecules are known to mediate cell:cell interactions and cell:molecule interactions. These include, for example, MHC proteins, cytokine, hormone or neurotransmitter receptors, tethered ligands, G-protein coupled receptors, receptor protein tyrosine kinases, receptor protein tyrosine phosphatases, protein-serine/threonine kinases and receptor guanylyl cyclases.

Most of the proteins that mediate cell-cell recognition and antigen recognition in the immune system contain Ig or Ig-like domains, suggesting that they have a common evolutionary history. These include antibodies, T cell receptors, cluster of differentiation (CD) antigens such as the CD4, CD8, and CD28 proteins, the invariant polypeptide chains associated with B and T cell receptors and Fc receptors on lymphocytes and other white blood cells. About half of the proteins that have been characterized on the surface of white blood cells belong to this superfamily. Cells of the immune system thus express a range of cell surface proteins whose identity can be used to evaluate the number and status of different cells in a sample.

B and T lymphocytes, for example, may be identified using antibodies to the constant regions of the B- and T-cell antigen receptors. T-helper and cytotoxic T-cells cells may be identified on the basis of expression of the co-receptor proteins, CD4 and CD8, respectively.

Flow cytometry is a powerful tool for identifying and enumerating cells. The flow cytometer detects and counts individual cells passing in a stream through a laser beam. By examining large numbers of cells, flow cytometry can give quantitative data on the percentage of cells bearing different molecules, such as surface immunoglobulin, which characterizes B cells, the T-cell receptor-associated molecules known as CD3, and the CD4 and CD8 co-receptor proteins that distinguish the major T-cell subsets. Individual cells within a mixed population are tagged with specific antibodies labelled with fluorescent dyes, or for example, by specific antibodies followed by labelled anti-immunoglobulin antibodies. The suspended mixture of labelled cells is then forced through an aperture, creating a fine stream of liquid containing cells spaced singly at intervals. As each cell passes through a laser beam it scatters the laser light, and any dye molecules bound to the cell will be excited and will fluoresce. Sensitive photomultiplier tubes detect both the scattered light, which gives information on the size and granularity of the cell, and the fluorescence emissions, which give information on the binding of the labelled antibodies and hence on the expression of cell-surface proteins by each cell. If two or more antibodies are used, each coupled to a different fluorescent dye, then the data may be displayed in the form of a two-dimensional scatter diagram or as a contour diagram, where the fluorescence of one dye-labelled antibody is plotted against that of a second, with the result that a population of cells labelling with one antibody can be further subdivided on the basis of its reactivity with the second antibody.

Immunoassays are another particularly useful form of assay that exploit the specificity, strength and diversity of antibody-antigen reactions to analyze samples and detect specific components therein. A wide range of immunoassay techniques are available, such as those described in Wild D. "*The Immunoassay Handbook*" Nature Publishing Group, 2001.

A wide range of methods for the detection of antibody to specific antigens are also known. For example, the enzyme-linked immunosorbent assay (ELISA) and radio-immunoassay (RIA) are routinely used in laboratories. Arrays and high throughput screening methods are also employed. These methods generally require a high level of skill in laboratory techniques.

A variety of methods have also been developed which require little skill and are rapid to perform, and which are therefore suitable for the detection of antibody to specific antigens, and/or the detection of specific antigens, at the point of care. In particular, lateral flow, dipstick and capillary tube kits have been developed to assay for a number of infections including viral infections.

In subjects with an immunodeficiency disease such as AIDS, the level of CD4 expressing T-cells is an indication of when to commence anti-retroviral drug treatment. The virus infects these T cells and ultimately destroys them. Low CD4$^+$ T-cell levels are also an indication of the risk of clinical progression and susceptibility to opportunistic infection.

In one method of detecting CD4 cells, dynabeads coated with anti-CD4 antibodies are used to bind CD4+ T-lymphocytes. Monocytes, that express CD14 and CD4, are excluded from fresh blood samples sample using beads coated with anti-CD14 antibodies. Thereafter, the isolated CD4 T-lymphocytes are lysed, stained with acridine orange and stained nuclei are enumerated by fluorescence microscopy. A "TRAx CD4" test kit is described in Paxton et al., Clin. Diagn. Lab. Immunol., 2(1):104-114, 1995. This kit is an ELISA based method to measure total CD4 in whole blood samples. The antibodies used did not distinguish between cell bound and soluble CD4 (see Lyamuya et al., J. Imm Methods, 195:103-112, 1996). International Publication No. WO 2006/115866 describe an immunochromatographic device for measuring CD4 antigens. However, again there is no disclosure in this document of a capture reagent capable of distinguishing between cell bound and soluble CD4 lacking a cytoplasmic domain in sample from a subject. Further, the device described in WO 2006/115866 depends upon the flow of sample over a series of numbered capture areas to capture CD4 by saturating consecutive capture areas on a test strip to subsequently provide a visual indication of the concentration of CD4 cells in the sample.

There is a need for improved methods of measuring particular cell types or their cell associated proteins, particularly methods that can be used at point of care and that provide rapid and accurate results.

SUMMARY

Throughout this specification and the claims which follow, unless the context requires otherwise, the word "comprise", and variations such as "comprises" and "comprising", will be understood to denote the inclusion of a stated integer or step or group of integers or steps but not the exclusion of any other integer or step or group of integers or steps. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are optional and may or may not be present depending upon whether or not they affect the activity or action of the listed elements.

It must be noted that, as used in the subject specification, the singular forms "a", "an" and "the" include plural aspects unless the context clearly dictates otherwise. For example, reference to a "sample pad" includes one sample pad or more than one sample pad.

Each embodiment in this specification is to be applied mutatis mutandis to every other embodiment unless expressly stated otherwise.

Nucleotide and amino acid sequences are referred to by a sequence identifier number (SEQ ID NO:). The SEQ ID NOs: correspond numerically to the sequence identifiers <400>1 (SEQ ID NO:1), <400>2 (SEQ ID NO:2), etc. A summary of sequence identifiers is provided in Table 1. A sequence listing is provided after the claims.

In a broad embodiment, the present specification describes method for evaluating in a sample from a subject the level or presence of a cell surface associated protein (CSAP) comprising a cytoplasmic (cytosolic) and an extracellular (ecto) domain or the level or presence of cells bearing the CSAP, the method comprising: (i) optionally contacting the sample with an agent capable of lysing or permeabilizing CSAP bearing cells; (ii) contacting the sample with a CSAP-binding agent that binds to the cytoplasmic domain of the CSAP; and (iii) directly or indirectly evaluating the level or presence of bound CSAP in the sample. In some embodiments the level or presence of bound CSAP comprising at least a cytoplasmic domain is indicative of the number of CSAP bearing cells in the subject.

In another embodiment, the specification describes a method for evaluating in a sample from a subject the level a cell surface associated protein (CSAP) comprising a cytoplasmic (cytosolic) and an extracellular (ecto) domain or the level of CSAP-bearing cells, the method comprising: a) applying the test sample to a sample portion of an immunochromatographic device wherein the sample portion is operably connected to a capture portion of the device and wherein components of the test sample flow from the sample portion to and through the capture potion which comprises an antibody or antigen-binding fragment thereof that binds to the cytoplasmic domain of CSAP such that only CSAP comprising a cytoplasmic domain and not soluble CSAP that does not comprise a cytoplasmic domain binds to the antibody or fragment thereof to form a captured CSAP; b) contacting the capture portion with a second binding agent that binds to CSAP including to the cytoplasmic or extracellular domain and which comprises a detection marker or which is capable of binding to a third or subsequent binding partner comprising a detection marker; c) optionally contacting the second binding agent with a third or subsequent binding agent comprising a detection marker; evaluating the presence of the detection marker.

In an illustrative embodiment, the method is used for evaluating in a blood sample from a subject the level of T-cell associated CD4 comprising a cytoplasmic (cytosolic) and an extracellular (ecto) domain or the level of CD4 T-cells, the method comprising: (i) optionally contacting the sample with an agent capable of lysing or permeabilizing CD4 T-cells; (ii) contacting the sample with an antibody or antigen-binding fragment thereof that binds to the cytoplasmic domain of CD4; and (iii) directly or indirectly evaluating the level or presence of bound CD4 in the sample.

In another embodiment of this aspect, the method is for evaluating from a subject the level of T-cell associated CD4 comprising a cytoplasmic (cytosolic) and an extracellular (ecto) domain or the level of CD4 T-cells and comprises: a) applying the test sample to a sample portion of an immunochromatographic device wherein the sample portion is operably connected to a capture portion of the device and wherein components of the test sample flow from the sample portion to and through the capture potion which comprises an antibody or antigen-binding fragment thereof that binds to the cytoplasmic domain of CD4 such that only CD4 comprising a cytoplasmic domain and not soluble CD4 that does not comprise a cytoplasmic domain binds to the antibody or fragment thereof to form a captured CD4; b) contacting the capture portion with a second binding agent that binds to CD4 including to the cytoplasmic or extracellular domain and which comprises a detection marker or which is capable of binding to a third or subsequent binding partner comprising a detection marker; and c) optionally contacting the second binding agent with a third or subsequent binding agent comprising a detection marker; evaluating the presence of the detection marker.

The agent that binds to the cytoplasmic domain of a CSAP or a sCSAP may be any form of molecule that specifically binds to a CSAP. CSAP-binding agents such as a ligand, aptamer or an antibody are particularly contemplated. Antibodies or an antigen binding fragments thereof are conveniently prepared with high specificity for a portion of a CSAP. In addition, antibodies can be conveniently conjugated to or produced with detectable markers or bound by secondary or subsequent antibodies conjugated to detectable markers. Either form of antibody whose function is directly or indirectly to detect an agent-CSAP complex may be referred to as a detection antibody.

In another broad embodiment, the method comprises (i) optionally contacting the sample with an agent capable of lysing or permeabilizing CSAP bearing cells, (ii) contacting the sample to be tested with an agent that binds to the extracellular domain of the CSAP such that both full length (CSAP) and a soluble form of the CSAP (sCSAP) are bound by the agent and form complexes comprising agent-CSAP and/or agent-sCSAP (iii) optionally, if the agent is not already bound to or associated with a region of a solid or semi-solid support, contacting the sample with a solid or semi-solid support such that the agent and any agent-CSAP complex and/or agent-sCSAP complex is bound to the solid-support (iii) contacting the sample or appropriate region of the support with a second agent that specifically binds to the cytoplasmic domain of the CSAP and (iv) directly or indirectly determining the presence or level of the bound second agent.

In another broad embodiment, the present specification provides a method for determining in a sample from a subject a) the level or presence of a protein expressed on the surface of a cell (CSAP) comprising a cytoplasmic (cytosolic) and an extracellular (ecto) domain or cells bearing the CSAP and b) the level of presence of a soluble non-membrane bound extracellular form of the CSAP (sCSAP) in the sample to be tested. The method comprises (i) optionally contacting the sample to be tested with an agent capable of lysing or permeabilizing CSAP bearing cells, (ii) contacting the sample with an agent that binds to the cytoplasmic domain of the CSAP and a second agent that binds the soluble form of CSAP lacking a cytoplasmic domain, (iii) directly or indirectly evaluating the level of bound CSAP and bound sCSAP in the sample. In embodiments where the level of sCSAP is also measured, the evaluation step (iii) distinguishes between agent-CSAP complexes and agent-sCSAP complexes. In this embodiment, the relative presence or amount of cell bound and soluble sCSAP in the sample from a subject may be determined.

In another aspect, the subject specification describes kits for detecting or monitoring the number of cells in sample from a subject, wherein the cell is characterised by comprising a cell surface associated protein (CSAP) comprising a cytoplasmic (cytosolic) and an extracellular (ecto) domain. In a broad embodiment, the kit comprises: (i) a chromatographic device comprising a porous membrane operably connected to a sample portion, a test (capture) portion, a conjugate portion, a sucker portion, optionally a control portion and optionally a lysis portion; (ii) a CSAP-binding agent such as an antibody or antigen-binding fragment thereof that binds to the cytoplasmic domain of CSAP, wherein the agent or antibody is either immobilised (bound) to one or more test portions and/or contained within a conjugate portion; and (iii) instructions for using the device to detect or monitor the level or presence of CSAP-bearing cells in the sample or subject.

In an illustrative embodiment, a kit for detecting or monitoring the number of CD4 T-cells in a blood sample from a subject is provided. In a broad embodiment, the kit comprises: (i) a chromatographic device comprising a porous membrane operably connected to a sample portion, a test (capture) portion, a conjugate portion, a sucker portion, optionally a control portion and optionally a lysis portion; (ii) a CD4-binding agent such as an antibody or antigen-binding fragment thereof that binds to the cytoplasmic domain of CD4, wherein the agent or antibody is either immobilised (bound) to one or more test portions and/or contained within a conjugate portion; and (iii) instructions for using the device to detect or monitor the level or presence of CD4 cells in the sample or subject. As will be appreciated by those of skill in the art of immunochromatography devices, the subject kits may be designed in any suitable format including reverse or lateral flow immunochromatography formats.

The above summary is not and should not be seen in any way as an exhaustive recitation of all embodiments of the present invention.

BRIEF DESCRIPTION OF THE FIGURES

FIGS. 3A and 3B represent the results from sheep G-6 and sheep G-7, respectively. Blood was samples pre-bleed (PB), in two test bleeds (TB1 and TB2) and a final bleed (FB).

FIG. 7 is a graphical representation of the results of flow cytometry analyses conducted to assess the ability of anti CD4$_{cyto}$ monoclonal antibodies ID2 and 4B4 to bind to fixed/permeabilized CD4+ T-cells (A, B, C, D). Antibodies bound to fixed/permeabilized cells and 92% of CD4+ cells were selected.

FIG. 8 is a schematic representation of two immunoassay formats suitable for the practice of the present invention.

FIG. 15 (B) is a representation of a sample device whereby CD4 T-cell numbers in a test strip can be estimated by comparing the intensity of staining of the test strip with standards representing 250, 350, and 500 cells per microlitre, respectively.

FIG. 16 is a representation of the nucleic acid sequence encoding one form of TM CD4 (SEQ ID NO:6). Underlined text is the His tag. Boxed text is the enterokinase recognition site. Bold text is the extracellullar domain of CD4 and Italics text is the cytoplasmic tail of CD4.

FIG. 17 is a representation of the amino acid sequence of one form of TM CD4 (SEQ ID NO:8). Underlined text is the His tag. Boxed text is the enterokinase recognition site. Bold text is the extracellullar domain of CD4 and Italics text is the cytoplasmic tail of CD4.

FIG. 19 is a graphical and photographic representation of data showing detection of TM^CD4 by ELISA and immunochromatographic rapid, point of care assay. Supernatant from HEK293 cells stably transfected with the TM^CD4 plasmid were serially diluted (starting at 1:5 dilution) for assay by ELISA (A), showing a linear response in the ELISA demonstrating the utility of the TM^CD4 as a control reagent for estimating total CD4 T-cell numbers in the CD4 ELISA assay. In this Figure, four different samples of whole blood were tested in the same assay (samples IDS72, 51, 40, 49), and the relative amount of CD4 compared to the standard can be estimated using the regression curve shown, or other methods. To enable conversion of the amount of CD4 to the number of CD4 T-cells per microlitre, a reference sample of whole blood was tested multiple times by flow cytometry and ELISA in comparison with the TM^CD4 standard, allowing the correct conversion factor to be determined (data not shown). (B) Supernatant from two different stable HEK293-TM^CD4 cell line clones (H5 and F5) were detected by rapid point of care assay, showing that TM^CD4 can be used as a control reagent or standard in such assays.

FIG. 22 is a photographic representation of results in the rapid immunographic device. (A) provides test results for rapid point of care assay format, using purified T-cells at the indicated numbers of cells per microlitre (reacting at Test lines). (B): Control lines were prepared to be equivalent to 500 T-cells/microlitre and 250 T-cells/microlitre, by striping biotinylated monoclonal antibody that reacts directly with the anti-biotin gold conjugate.

Figure 1:
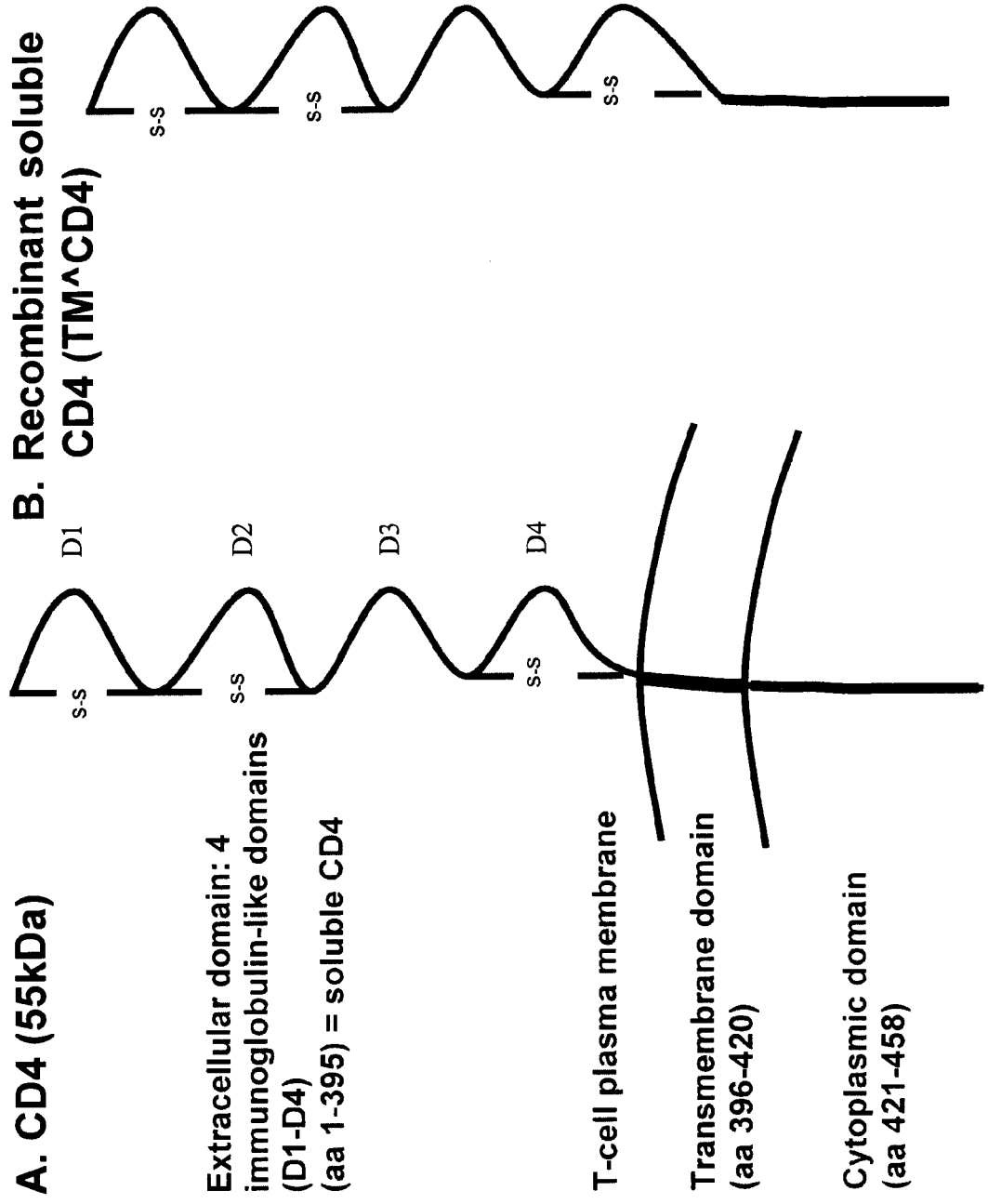
FIG. 1(A) is a schematic representation of human CD4 associated with a T-lymphocyte cell surface membrane. The extracellular domain comprising amino acids 1-395 is shown, arranged as four immunoglobulin-like domains together with disulphide bonded regions thereof. The transmembrane domain comprising amino acids 396-420 is shown spanning the T-lymphocyte cell surface membrane. The cytoplasmic (cytosolic) domain comprising amino acids 421-458 is also illustrated.
FIG. 1(B) represents the structure of TM^CD4 comprising a cytoplasmic and extracellular domain and with a deletion of the transmembrane domain plus the first two amino acids of the cytoplasmic domain, such that this TM^CD4 protein represents amino acids 1-395 fused to amino acids 423-458.

In the Figure, purified monocytes and purified peripheral blood leucocytes (PBLs, depleted of monocytes) were separately labelled with infrared fluorescent dyes—monocytes with green (Mini CellVue NIR815, PTI Research, Inc), PBLs with red (Mini CellVue Burgundy, PTI Research Inc.). The images display the same sample pads viewed through different filters on the Licor Odyssey infrared fluorescent scanner: (A)=combined filters, (B)=Em 800, (C)=Em 700. The magnet obscures scanning of the sample pad where it is used. $1.5 \times 10^4$ monocytes (attached to magnetic beads) and $2 \times 10^4$ monocyte depleted PBLs were combined and spotted onto anti-glycophorin A coated sample pads either without (left) or with the magnet (right). Sample was flushed with 60 ul PBS to allow sample to flow into the absorbent pad (used here instead of an actual lysis pad and nitrocellulose test strip for illustrative purposes). Retention of >80% monocytes (green) can be seen in panel (A) and (B) in the presence of a magnet, with no green cells entering the absorbent pad, whilst flow-through of monocyte-depleted PBLs into the absorbent pad is demonstrated in (A) and (C) in both the presence or absence of a magnet. (D) shows a schematic description of the test as shown in (A)-(C).

BRIEF DESCRIPTION OF THE TABLES

Table 1 provides a description of the SEQ ID NOs provided herein.
Table 2 provides an amino acid sub-classification.
Table 3 provides exemplary amino acid substitutions.

DETAILED DESCRIPTION OF THE PREFERRED EMBODIMENTS

In the work leading up to the present invention, the inventors have developed a strategy for accurately enumerating specific cell types in cellular samples from a subject. The invention is predicated, in part, upon the recognition that prior art methods for detecting proteinaceous markers for particular cell types employ agents that bind to the extracellular portion of a cell marker. As many cell surface associated molecules are present in both cell associated and soluble forms, these agents detect soluble forms of the marker leading to false positives or an overestimation of the number of a particular cell type. In some embodiments, the method does not detect soluble CSAP lacking a cytoplasmic domain which may be present in the sample. In other embodiments, the method distinguishes between cell associated CSAP comprising an cytoplasmic domain and soluble CSAP lacking a cytoplasmic domain.

In some embodiments, the invention provides assays such as immunoassays comprising agents that distinguish between soluble and full length forms of cell surface markers. In a particularly useful embodiment of the invention, rapid point of care (RPOC) methods and kits are provided that require no sample processing, microscopy, other instrumentation or scientific expertise.

Accordingly, in one embodiment, the present invention provides a method for evaluating in a sample from a subject the level or presence of a cell surface associated protein (CSAP) comprising a cytoplasmic (cytosolic) and an extracellular (ecto) domain or cells bearing the CSAP, the method comprising (i) optionally contacting the sample with an agent capable of lysing or permeabilizing CSAP bearing cells, (ii) contacting the sample with an agent that binds to the cytoplasmic domain of the CSAP (iii) directly or indirectly evaluating the level of bound CSAP in the sample. In accordance with this aspect of the present invention, the method permits the detection or measurement of cell-bound CSAP in a sample that also comprises soluble CSAP. The level of agent-CSAP complexes can be used to qualify the presence of a specific cell bound CSAP or quantify the amount of a specific cell bound CSAP molecule in the sample. Using information concerning how many CSAP molecules are on average present on the surface of the specific cell type it is possible to estimate the number of cells bearing CSAP that are present in the sample.

The agent that binds to the cytoplasmic domain of a CSAP or the soluble form of CSAP may be any CSAP-binding agent such as a ligand, aptamer or antibody, however specific antibody or an antigen binding fragments thereof are conveniently prepared. In particular, antibodies can be conveniently conjugated to or produced with detectable markers or bound by secondary or subsequent antibodies conjugated to detectable markers.

Immunoassays can be done in any convenient format known in the art. These include Western blots, immunohistochemical assays and ELISA assays. The use of monoclonal antibodies in an immunoassay is particularly preferred because of the ability to produce them in large quantities and the homogeneity of the product. However, as shown herein, polyclonal antibodies may also be used. The preparation of hybridoma cell lines for monoclonal antigen production is derived by fusing an immortal cell line and lymphocytes sensitized against the antigen of interest (in a non-limiting example the antibody is in the case of CD4 polypeptides, peptides 1 or 2 or homologs, derivatives, variants thereof) or can be done by techniques which are well known to those who are skilled in the art. (See, for example, Douillard and Hoffman, Basic Facts about Hybridomas, in *Compendium of Immunology* Vol. II, ed. by Schwartz, 1981; Kohler and Milstein, *Nature* 256: 495-499, 1975; *European Journal of Immunology* 6: 511-519, 1976 or more recent references Sambrook, *Molecular Cloning: A Laboratory Manual*, 3$^{rd}$ Edition, CSHLP, CSH, NY, 2001).

Another aspect of the present invention contemplates a method for detecting a CSAP in a biological sample from a subject, said method comprising contacting said biological sample with an antibody specific for the cytoplasmic domain of the CSAP for a time and under conditions sufficient for an antibody-CSAP complex to form, and then detecting said complex.

The presence of CSAP may be evaluated in a number of ways such as by Western blotting and ELISA procedures. A wide range of immunoassay techniques are available as can be seen by reference to U.S. Pat. Nos. 4,016,043, 4,424,279 and 4,018,653. These include both single-site and two-site or "sandwich" assays of the non-competitive types, as well as in the traditional competitive binding assays.

Sandwich assays are among the most useful and commonly used assays and are favoured for use in the present invention. A number of variations of the sandwich assay technique exist, and all are intended to be encompassed by the present invention. Briefly, in a typical forward assay, an antibody is immobilized on a solid or semi-solid substrate and the sample to be tested brought into contact with the bound molecule. After a suitable period of incubation, for a period of time sufficient to allow formation of an antibody-antigen complex, a second antibody specific to the antigen, labelled with a reporter molecule capable of producing a detectable signal is then added and incubated, allowing time sufficient for the formation of another complex of antibody-antigen-labelled antibody. Any unreacted material is washed away, and the presence of the CSAP is determined by observation of a signal produced by the detectable marker (reporter molecule). The results may be qualitative or quantitative, by simple observation of the visible signal, or may be quantitated by comparing with a control sample containing known amounts of CSAP. Variations on the forward assay include a simultaneous assay, in which both sample and labelled antibody are added simultaneously to the bound antibody. These techniques are well known to those skilled in the art, including any minor variations as will be readily apparent. In accordance with the present invention, the sample is one which might contain a CSAP, such as a cell extract or tissue biopsy. The sample is, therefore, generally a biological sample comprising biological fluid.

In a typical forward sandwich assay, a first antibody having specificity for the cytoplasmic domain of CSAP is either covalently or passively bound to a solid or semi-solid support. The support is typically glass or a polymer, the most commonly used polymers being nitrocellulose, cellulose, polyacrylamide, nylon, polystyrene, polyvinyl chloride, polypropylene or mixture or derivatives of these. The solid supports may be in the form of tubes, beads, discs or microplates, or any other surface suitable for conducting an immunoassay. The binding processes are well-known in the art and generally consist of cross-linking covalently binding or physically adsorbing the polymer-antibody complex to the solid surface which is then washed in preparation for the test sample. An aliquot of the sample to be tested is then added to the solid phase complex and incubated for a period of time sufficient (e.g. 2-40 minutes or overnight if more convenient) and under suitable conditions (e.g. from room temperature to about 37° C. including 25° C.) to allow binding of any subunit present in the antibody. Following the incubation period, the antibody subunit solid phase is washed and incubated with a second antibody specific for a portion of the antigen. The second antibody is linked to a detectable marker which is used to indicate the binding of the second antibody to the antigen.

An alternative method involves immobilizing the target molecules in the biological sample and then exposing the immobilized target to specific antibody which may or may not be labelled with a detectable marker. Depending on the amount of target and the strength of the signal from the detectable marker, a bound target may be detectable by direct labelling with the antibody. Alternatively, a second labelled antibody, specific to the first antibody is exposed to the target-first antibody complex to form a target-first antibody-second antibody tertiary complex. The complex is detected by the signal emitted by the reporter molecule. A significant improvement of the bead-based methods involves tagging each bead with a unique identifier tag, such as an oligonucleotide or electrophoretic tag, so as to facilitate identification of the amino acid sequence of each library member. These improved bead-based methods are described in International Publication No. WO 93/06121.

In other embodiments, the method is a liquid phase method. In one example of a liquid phase immunoassay (see for example U.S. Pat. No. 6,632,603) the sample is contacted with an agent capable of binding the cytoplasmic portion of a CSAP and a detector agent comprising a visually detectable agent such as colloidal gold or silver labelled. The test sample is applied by flowing onto a defined zone of an insoluble porous support film having a pore size impassable to a complex formed between the CSAP, if present, with the binding substance and the detector substance, but passable to the binding substance and detector substance while remaining uncomplexed in the absence of the desired CSAP. If the CSAP is present in the test specimen, the detector substance binds with the CSAP and the binding substance to form a visually inspectable complex on the surface of the porous support film. After application of the test sample to the porous support, the surface of the porous support is visually inspected for colour to determine the presence and quantity or the absence of the CSAP being assayed.

In another assay, magnetic antibodies that bind to CSAP markers are used to tag CSAP and a high $T_c$ superconducting quantum interference device is used to measure the amount of free and bound antibody and hence the presence or level of CSAP. A liposome immunomigration, liquid-phase competition strip immunoassay is, for example, described in Glorio-Paulet et al *J Agric Food Chem* 48 (5):1678-1682, 2000.

General formats and protocols for the conduct of various formats of ELISA are disclosed in the art and are know to those of skill in the field of diagnostics. For example, reference may be made to Chapter 11 of Ausubel (Ed) *Current Protocols in Molecular Biology*, $5^{th}$ Edition, John Wiley & Sons, Inc, NY, 2002.

In a further preferred embodiment, the agent that binds to the cytoplasmic domain of the CSAP serves to attach the CSAP to a solid or semi-solid support. This allows any soluble CSAP in the sample to be physically separated from the CSAP, which may then be detected with agents that bind to the extracellular domain of the CSAP.

In another embodiment, the method comprises (i) optionally contacting the sample with an agent capable of lysing or permeabilizing CSAP bearing cells, (ii) contacting the sample to be tested with an agent that binds to the extracellular domain of the CSAP such that both CSAP and soluble forms of the CSAP are bound by the agent and form complexes comprising agent-CSAP and/or agent-sCSAP (iii) optionally, if the agent is not already bound to or otherwise associated with a region of a solid or semi-solid support, contacting the sample with a solid or semi-solid support such that the agent and any agent-CSAP complex and/or agent-sCSAP complex is bound to the solid-support (iii) contacting the sample with a second agent that specifically binds to the cytoplasmic domain of the CSAP and (iv) directly or indirectly determining the presence or level of bound second agent.

In another embodiment, the present invention provides a method for determining in a sample from a subject a) the level or presence of a protein expressed on the surface of a cell (CSAP) comprising a cytoplasmic (cytosolic) and an extracellular (ecto) domain or cells bearing the CSAP and b) the level of presence of a soluble non-membrane bound extracellular form of the CSAP in the sample. In this embodiment, the sample is further contacted with an agent that binds the soluble form of CSAP. In embodiments where the level or presence of soluble CSAP is also measured, the evaluation step (iii) distinguishes between agent-CSAP complexes and agent-sCSAP complexes. In this embodiment, the relative presence or amount of cell bound and soluble CSAP in the sample from a subject may be determined.

In some embodiments, the method comprises (i) applying a sample from a subject to a portion of a chromatographic or immunographic device bearing an antibody that specifically binds to the cytoplasmic domain of a CSAP such that substantially only cell bound CSAP comprising a cytoplasmic portion is captured onto the test portion. In some embodiments, where the presence or level of soluble CSAP is required to be detected, another portion of the chromatographic device bears an antibody that binds soluble CSAP such that any soluble CSAP is captured onto further test portions of the chromatographic device. Of course, an antibody that binds to the extracellular domain of soluble CSAP will also be capable of binding to the extracellular domain CSAP. However, if all the CSAP present in the sample is bound to other portions of the device via antibodies to the cytoplasmic domain, the anti-soluble CSAP antibody will bind only soluble forms of the CSAP.

In some embodiments, the sample to be tested comprises cells derived from the body, such as, spinal fluid, bone or tissue samples, serum, plasma, saliva, tears and milk. In some embodiments, the test sample is whole blood or diluted whole blood is a derivative of whole blood. Blood may, in some embodiments, be maintained in the presence of an anticoagulant such as heparin, sodium citrate or ethylene diamine tetra acetic acid (EDTA).

In one or more of the above described methods the detection step comprises contacting the bound CSAP with a second binding agent that binds to the CSAP and which comprises a detection marker or which is capable of binding to a third binding agent comprising a detection marker and detecting the detection marker. In some especial embodiments the CSAP-binding agent is an antibody or antigen binding fragment thereof. Similarly, in some embodiments the second binding agent is an antibody or antigen-binding fragment thereof which binds to CSAP including to the cytoplasmic or extracellular domain of the CSAP.

As mention above, an especial embodiment of the method comprises evaluating the number of CSAP bearing cells in the sample. In some embodiments, this is achieved by comparison of the level or presence of bound CSAP or the level or presence of bound detection marker with a predetermined control. In some embodiments, the predetermined control is a predetermined amount of a control polypeptide sufficient to produce, when bound to a visual detection marker, a signal providing a internal visual reference equivalent to the signal produced by a predetermined number of CSAP cells.

The method for evaluating cells will depend upon the format of the method used and ELISA type, flow cytometry or chromatographic methods are all contemplated. In some embodiments where the method is an ELISA or chromatographic method the CSAP-binding agent that binds to the cytoplasmic domain of CSAP is immobilised on a solid or semi-solid support. In other embodiments, the method is an ELISA or chromatographic method and the second binding agent that binds to the CSAP including to the cytoplasmic or extracellular domain of CSAP is immobilised on a solid or semi-solid support.

The method is suitable for use in an immunochromatographic device. In some embodiments of this aspect there is provided a method for evaluating in a sample from a subject the level a cell surface associated protein (C SAP) comprising a cytoplasmic (cytosolic) and an extracellular (ecto) domain or the level of CSAP-bearing cells. In some embodiments, the method comprises: a) applying the test sample to a sample portion of an immunochromatographic device wherein the sample portion is operably connected to a capture portion of the device and wherein components of the test sample flow from the sample portion to and through the capture potion which comprises an antibody or antigen-binding fragment thereof that binds to the cytoplasmic domain of CSAP such that only CSAP comprising a cytoplasmic domain and not soluble CSAP that does not comprise a cytoplasmic domain binds to the antibody or fragment thereof to form a captured CSAP; b) contacting the capture portion with a second binding agent that binds to CSAP including to the cytoplasmic or extracellular domain and which comprises a detection marker or which is capable of binding to a third or subsequent binding partner comprising a detection marker. In some embodiments, the method further comprises c) optionally contacting the second binding agent with a third binding agent comprising a detection marker; evaluating the presence of the detection marker. Of course, further binding partners may be employed, if required.

In an illustrative embodiment, the specification provides a method for evaluating in a blood sample from a subject the level of T-cell associated CD4 comprising a cytoplasmic (cytosolic) and an extracellular (ecto) domain or the level of CD4 T-cells, the method comprising: (i) optionally contacting the sample with an agent capable of lysing or permeabilizing CD4 T-cells; (ii) contacting the sample with an antibody or antigen-binding fragment thereof that binds to the cytoplasmic domain of CD4; and (iii) directly or indirectly evaluating the level or presence of bound CD4 in the sample. In some embodiments, step (iii) comprises contacting the CD4-antibody complex with a second antibody or antigen-binding fragment thereof that binds to CD4 including to the cytoplasmic or extracellular domain and which comprises a detection marker or which is capable of binding to a third binding partner comprising a detection marker, and detecting the detection marker. In some embodiments, the method comprises determining the number of CD4 bearing cells in the sample by comparison of the level or presence of bound CD4 or bound detection marker with a predetermined control. In some embodiments, the predetermined control is a predetermined amount of a control polypeptide sufficient to produce, when bound to a visual detection marker, a signal providing a internal visual reference equivalent to the signal produced by a predetermined number of CD4 cells. As above however, in some embodiments, the method is an ELISA, flow cytometry or chromatographic method.

In some embodiments, the method is an ELISA or chromatographic method and the antibody or antigen-binding fragment thereof that binds to the cytoplasmic domain of CD4 (anti-cytoCD4 antibody) is immobilised on a solid or semi-solid support.

In relation to chromatographic devices, many different formats are available. however, in one embodiment a method for evaluating in a blood sample from a subject the level of T-cell associated CD4 comprising a cytoplasmic (cytosolic) and an extracellular (ecto) domain or the level of CD4 T-cells is provided. In some embodiments, the method comprising: a) applying the test sample to a sample portion of an immunochromatographic device wherein the sample portion is operably connected to a capture portion of the device and wherein components of the test sample flow from the sample portion to and through the capture potion which comprises an antibody or antigen-binding fragment thereof that binds to the cytoplasmic domain of CD4 such that only CD4 comprising a cytoplasmic domain and not soluble CD4 that does not comprise a cytoplasmic domain binds to the antibody or fragment thereof to form a captured CD4; b) contacting the capture portion with a second binding agent that binds to CD4 including to the cytoplasmic or extracellular domain and which comprises a detection marker or which is capable of binding to a third or subsequent binding partner comprising a detection marker; c) optionally contacting the second binding agent with a third or subsequent binding agent comprising a detection marker; evaluating the presence of the detection marker.

For the control polypeptide, in some embodiments the control polypeptide is CD4 polypeptide comprising at least cytoplasmic domain. Regarding the number of CD4 cells, in some embodiments this is one or more of less than 200, less than 250, more than 250, 250 to 350, 350 to 500, 250 to 500 and more than 500 cells/µl of blood. In other embodiments, the number of CD4 T-cells is one or more of less than 200, less than 500, 500 to 1,000, 1,000 to 2,000, and more than 2,000 cells/µl of blood.

Various methods are available for depleting monocytes or red blood cells from blood cells, if required. In some embodiments, monocytes in the sample are depleted by contacting the sample with anti-CD 14 antibodies bound to a solid or semi-solid support. In another embodiment, red blood cells are depleted in the sample by contacting the sample with anti-glycophorin antibodies bound to a solid or semi-solid support.

In another aspect, the present invention provides a device or kit suitable for the practice of the subject methods.

In some embodiments, a chromatographic device is provided comprising material which has a pore size which allows or facilitates capillary flow of the components of the method. In some embodiments, the device comprises portions comprising material of different pore size, or non-porous material, the material being contiguous with the first material and designed to receive a sample or receive or store components of the method. In some embodiments, the portions of the chromatographic device are separate, contiguous or overlapping or designed to come together in use.

In some embodiments, the sample pad is chromatographically connected to a test portion of the device, the test portion comprising an antibody or an antibody binding fragment thereof. In an illustrative embodiment, the subject is a mammal and the test portion comprises an antibody which, under the appropriate conditions, recognizes and binds the cytoplasmic domain of a CSAP polypeptide.

In some embodiments, the sample pad is chromatographically connected to a test portion of the device, the test portion comprising an antibody or an antibody binding fragment thereof. In an illustrative embodiment, the subject is a mammal and the test portion comprises an antibody which, under the appropriate conditions, recognizes and binds the cytoplasmic domain of a protein comprising Ig or Ig-like domains.

In other embodiments, the CSAP is a receptor such as without limitation a cytokine, hormone or neurotransmitter receptors, a tethered ligand, G-protein coupled receptors, receptor protein tyrosine kinases, receptor protein tyrosine phosphatases, protein-serine/threonine kinases and receptor guanylyl cyclases.

In some embodiments, when chromatographically active portions of the sample to be tested move from the sample pad towards and through the test portion, CSAP comprising a cytoplasmic domain is captured onto test or control portions of the device and the remainder of the sample flowing from the sample pad is uncaptured. This arrangement ensures that essentially only the non-soluble CSAP to be detected in this embodiment is allowed to interact with detection antibodies, which may therefore be directed to soluble or non-soluble CSAP. In a preferred embodiment, the CSAP is detected with an antibody that binds to the extracellular domain of CSAP to avoid binding to sites used by the antibodies that bind to the cytoplasmic domain of the CSAP. In some embodiments, the uncaptured components of the test sample are collected chromatographically into an absorbent pad, which is positioned in any orientation with respect to the test portion. Components of the subject sample, such as red blood cells or particular white blood cells may be retained in the sample pad, for example, by selecting a pad of suitable mesh or pore size and/or by the inclusion of specific reagents such as antibodies or lectins to bind and retain these components. For example monocytes may be retained using anti-CD14 antibodies. Anti-glycophorin antibodies may be used to retain/remove red blood cells.

In some embodiments, once the test portion of the immunochromatographic device has been exposed to CSAP in the subject sample, the method proceeds by allowing contact between a detection marker and the test portion. In some embodiments, the detection marker is stored in a separate detection marker pad.

In some embodiments, the detection marker comprises a visually detectable reporter molecule and a positive result may be essentially immediately observed in the test and/or control portions of the immunochromatographic device. In other embodiments, the detection marker may be detected using further detection protocols and devices such as will be well known to those of ordinary skill in the art. For example, in addition to colloidal gold, as exemplified herein, other colloidal metal or metal oxide particles or colloidal non-metal particles or dyes or coloured latex are conveniently used.

In an illustrative embodiment, the specification describes kits for detecting or monitoring the number of cells in sample from a subject, wherein the cell is characterised by comprising a cell surface associated protein (CSAP) comprising a cytoplasmic (cytosolic) and an extracellular (ecto) domain. In some embodiments, the kit comprises: (i) a chromatographic device comprising a porous membrane operably connected to a sample portion, a test (capture) portion, a conjugate portion, a sucker portion, optionally a control portion and optionally a lysis portion; (ii) a CSAP-binding agent such as an antibody or antigen-binding fragment thereof that binds to the cytoplasmic domain of CSAP, wherein the agent or antibody is either immobilised (bound) to one or more test portions and/or contained within a conjugate portion; and (iii) instructions for using the device to detect or monitor the level or presence of CSAP-bearing cells in the sample or subject.

In a further non-limiting illustrative embodiment, the kit comprises: (i) a chromatographic device comprising a porous membrane operably connected to a sample portion, a test (capture) portion, a conjugate portion, a sucker portion, optionally a control portion and optionally a lysis portion; (ii) a CD4-binding agent such as an antibody or antigen-binding fragment thereof that binds to the cytoplasmic domain of CD4, wherein the agent or antibody is either immobilised (bound) to one or more test portions and/or contained within a conjugate portion; and (iii) instructions for using the device to detect or monitor the level or presence of CD4 cells in the sample or subject. Such kits may of course be presented any suitable format such as reverse or lateral flow immunochromatography formats. In preferred embodiments the conjugate portion comprises a visual detection marker. In other embodiments, the control portion comprises a pre-determined amount of a control polypeptide sufficient to produce, when bound to a visual detection marker, a signal providing an internal reference equivalent to the signal produced by a pre-determined number of cells. In some embodiments, the control portion comprises a pre-determined amount of a control CD4 polypeptide comprising at least a cytoplasmic domain and sufficient to produce, when bound to a visual detection marker, a signal providing a visual standard of a pre-determined number of CD4 cells. In some embodiments, the CD4 polypeptide is recombinant CD4 lacking a transmembrane domain.

For CD4 T cell evaluations, in some embodiments, the kits advantageously provide for a pre-determined number of one or more of: less than 200, less than 250, more than 250, 250 to 350, 350 to 500, 250 to 500 and more than 500 cells/µl of blood. Alternatively, the pre-determined number is one or more of: less than 200, less than 500, 500 to 1,000, 1,000 to 2,000, and more than 2,000 cells/µl of blood. Red blood cells and/or monocytes are deleted in some embodiments and kits employ reagents to effect red blood cell and/or monocyte depletion. In some embodiments, the sample pad comprises a red blood cell capture agent such as glycophorin A and/or anti-CD 14 magnetic beads other monocyte specific reagents.

In accordance with the present invention it has been determined that an inexpensive or disposable magnetic is effective in the present immunochromatographic strips to effect cell separation. In some embodiments, a magnet is used having a field strength extending less than about 5 mm through a sample. In some embodiments, a magnet is included in the kit. In some embodiments, the magnetic material is attached or attachable to the sample pad or to a portion of the immunochromatographic device capable of coming into contact with the sample pad.

In another embodiment, the number of CSAP-bearing cell is evaluated in a kit by: (i) applying the test sample from the subject to the sample portion under conditions in which the CSAP bearing cells will flow over the capture potion towards the sucker portion; (ii) directly or indirectly detecting the presence of captured CSAP in the capture portion using a visual detection marker; and (iii) comparing the intensity of the signal from the detection marker in (ii) with the intensity of the signal from the control portion comprising a control polypeptide providing an internal reference equivalent to the signal produced by a pre-determined number of CSAP bearing cells.

In some embodiments, the test sample is contacted with a lysis buffer or passes through a lysis portion capable of or for lysing or permeabilising CSAP bearing cells.

Recombinant CD4 lacking a transmembrane domain for use or suitable for use as a control in methods or kits to determine CD4 T-cell numbers. Accordingly, the present invention contemplates the use of recombinant CD4 lacking a transmembrane domain in the manufacture of a solid or semi-solid support or a kit for quantifying the number of CD4 T-cells in a sample from a subject.

In some embodiments, the subject methods and/or kits are for use in evaluating AIDS or other immunodeficiency disease patients.

In some embodiments, the subject is a human. The present invention extends, however, to primates, livestock animals, laboratory test animals, companion animals and avian species as well as non-mammalian animals such as reptiles. The method has applications, therefore in human, livestock, veterinary and wild-life therapy and diagnosis.

The present invention further provides a kit in compartmental form comprising reagents and a chromatographic device required to perform the subject method. Generally the kit further comprises a set of instructions.

Accordingly, in another aspect, the present invention provides a kit for evaluating in a sample from a subject the level or presence of a cell surface associated protein (CSAP) comprising a cytoplasmic (cytosolic) and an extracellular (ecto) domain or the level or presence of cells bearing the CSAP, the kit in compartmental form comprising an immunochromatographic device comprising portions for receiving the sample, portions for receiving or comprising a detection marker, together with test and control portions of the device comprising an agent such as an antibody or antigen binding fragment there of which binds to the cytoplasmic domain of a protein expressed on the surface of cell (CSAP). In some embodiments, the portions of the device are separate, contiguous or overlapping. In some embodiments, the kit uses reverse flow immunochromatography. In other embodiments, the kit uses lateral flow immunochromatography. In some embodiments, the CSAP is a marker for a particular cell type, such as an Ig or Ig-like domain comprising protein. In one embodiment, the cell marker is selected from the group comprising cluster of differentiation (CD) antigens. In an exemplified embodiment the CSAP is CD4. In this aspect of the invention, the level of CD4 or CD4 bearing cells is indicative of a subject's need for antiretroviral therapy. Specifically, in the case of subjects with HIV infections a level of less than about 200 cells/µl of blood or of less than about 250 cells/µl of blood is indicative that anti-retroviral therapy is required. In accordance with this aspect of the invention, an immunochromatographic device is provided that allows a quantitative estimate of CD4 T-cells in clinically useful ranges such as less than 250, more than 250, 250 to 350, 350 to 500, 250 to 500 and more than 500 cells/µl of blood. In some embodiments these ranges or amended versions thereof are useful monitoring HIV patients. In another embodiment, the device allows a quantitative estimate of CD4 T-cells of less than 500, 500 to 1,000, 1,000 to 2,000, and more than 2,000 cells/µl of blood suitable for monitoring pediatric HIV patients.

In another embodiment the CSAP is a receptor such as a receptor for a cytokine, hormone or neurotransmitter. In one preferred embodiment, the receptor is a TNF receptor.

Reference herein to the term "hematopoietic cell" encompasses undifferentiated hematopoietic stem cell (HSC) and any one or more of the blood cell types which arise from HSC. The term refers to multipotent cells as well as the various different forms of myeloid- or lymphoid-restricted cells that ultimately give rise to fully differentiated mature blood cells. In adults, HSC reside in the bone marrow, peripheral blood, lung, liver, spleen and other organs. HSC are the first in a hierarchy of progenitor cells. They are capable of long-term self renewal (long term (LT)-HSCs). LT-HSCs differentiate into short-term multipotent HSCs, (ST-HSCs) that retain the ability to produce all blood types but only proliferate for a relatively short time. Next, lymphoid progenitors arise that ultimately produce immune cells, and myeloid progenitors arise that ultimately produce mainly red blood cells and platelets and some innate immune cells. These progenitor cells have various abilities to proliferate and differentiate and from these cells ultimately arise terminally differentiated cells.

Accordingly, reference to HSC and hematopoietic progenitors include all the above mentioned progenitor cells and reference to hematopoietic or blood cells include any of their terminally differentiated descendants. These include without limitation: HSC, hematopoietic stem cell; CLP, common lymphoid precursor; CMP, common myeloid precursor; GMP, granulocyte-macrophage precursor; MEP, megakaryocyte-erythroid precursor; CFU-GM, colony forming unit-granulocytic/macrophage; CFU-G, colony forming unit-granulocytic; CFU-M, colony forming unit-macrophage; CFU-Mk, colony forming unit-megakaryocytic; BFU-e, Burst-forming unit erythroid; and CFU-E, colony forming unit-erythroid cells and their progeny.

Reference herein to a "CD" protein or polypeptide includes one or more CD antigens selected from the group comprising CD1a,b,c,d, CD2, CD3, CD4, CD5, CD6, CD7, CD8, CD9, CD10, CD11a, CD11b, CD11c, CD11d, CDw12, CD13, CD14, CD15, CD15s, CD15u, CD16, CDw17, CD18, CD19, CD20, CD21, CD22, CD23, CD24, CD25, CD26, CD28, CD29, CD30, CD31, CD32, CD33, CD34, CD35, CD36, CD37, CD38, CD39, CD40, CD41, CD42a,b,c,d, CD43, CD44, CD45, CD45RO, CD45RA, CD45RB, CD46, CD47, CD48, CD49a, CD49b, CD49c, CD49d, CD49e, CD49f, CD50, CD51, CD52, CD53, CD54, CD55, CD56, CD57, CD58, CD59, CD60a, CD60b, CD60c, CD61, CD62E, CD62L, CD62P, CD63, CD64, CD65, CD66a, CD66b, CD66c, CD66d, CD66e, CD66f, CD68, CD69, CD70, CD71, CD72, CD73, CD74, CD75, CD75s, CD77, CD79α,β, CD80, CD81, CD82, CD83, CDw84, CD85, CD86, CD87, CD88, CD89, CD90, CD91, CD92, CD93, CD94, CD95, CD96, CD97, CD98, CD97, CD100, CD101, CD102, CD103, CD104, CD105, CD106, CD107a, CD107b, CD108, CD109, CD110, CD111, CD112, CD114, CD115, CD116, CD117, CD118, CD119, CD120a, CD120b, CD121a, CDw121b, CD122, CD123, CD124, CD125, CD126, CD127, CDw128, CD129, CD130, CDw131, CD132, CD133, CD134, CD135, CDw136, CDw137, CD138, CD139, CD140a,b, CD141, CD142, CD143, CD144, CD145, CD146, CD147, CD148, CD150, CD151, CD152, CD153, CD154, CD155, CD156a, CD156b, CD157, CD158, CD158a, CD158b, CD159a, CD160, CD161, CD162, CD162R, CD163, CD164, CD165, CD166, CD167a, CD168, CD169, CD170, CD171, CD172a, CD173, CD174, CD175, CD175s, CD176, CD177, CD178, CD179a, CD179b, CD180, CD183, CD184, CD195, CDw197, CD200, CD201, CD202b, CD203c, CD204, CD205, CD206, CD207, CD208, CD209, CDw210, CD212, CD213a1, CD213a2, CDw217, CD220, CD221, CD222, CD223, CD224, CD225, CD226, CD227, CD228, CD229, CD230, CD231, CD232, CD233, CD234, CD235a, CD235b, CD236, CD236R, CD238, CD239, CD240CE, CD240D, CD241, CD242, CD243, CD244, CD245, CD246 and CD247. Such molecules and the cells upon which they are found are described in Janeway et al., *Appendix II. CD Antigens*, Immunology, Garland Publishing, New York, 5$^{th}$ edition, 2001, that is incorporated herein in its entirety by reference.

Reference herein to a "chromatographic device" includes a device of any solid, semi-solid, matrix or gel material which is known in the art for facilitating or supporting chromatographic flow or separation. As used herein, the components of the sample including antibodies, and the detection marker-antigen complex and components thereof are moved relative to each other by capillary flow or diffusion through chromatographic material. The material may be functionalized or coated to permit for example cross-linking of reagents. Methods for immobilizing antibodies to solid supports are well known in the art and are described for example in U.S. Pat. No. 4,168,146, Cautrecases *J. Biol. Chem.* 245: 3059, 1970. Materials contemplated for use herein include inorganic materials such as silica, glass, polymeric material such as cellulose, starch, dextrose, agarose, special fibrous paper (filter/chromatography paper) nitrocellulose, cellulose acetate, PVC, polyacrylamide, polysaccharide, polyacrylate, polyethylensulphonate, polyethylene and the like.

"Chromatographically active" components are simply those capable of flow through all or part of the immunochromatographic device.

Reference herein to "derived from" means that the sample is obtained from a particular source but not necessarily directly from that source.

"Antibodies" include immunoglobulin gene products that interact with an antigen i.e., an antigen-binding agent, fragments thereof and non-immunoglobulin gene derived proteinaceous molecules that are capable of serving as an antigen binding agent. The term antibody therefore, includes polyclonal and monoclonal antibodies and parts thereof including Fab portions and antigen-binding determinants. Immunoglobulin genes include κ, λ, α, γ, (IgG$_1$, IgG$_2$, IgG$_3$, IgG$_4$,) δ, ε, and μ constant regions and multiple variable region genes.

Typically an immunoglobulin comprises two identical pairs of immunoglobulin chains each pair comprising light chain ($V_L$) and heavy chain ($V_H$) variable portions which have antigen-binding regions. Each pair also comprises a constant region which provides generic antibody functions. Other forms of immunoglobulin are $F_v$, sc$F_v$, Fab, Fab$^1$, and (Fab$^1$)$_2$ forms. Reference a "class" of an antibody includes reference to any class such as IgM, IgG, IgA etc.

The ability to rapidly and accurately determine CD4$^+$ cell levels is important for assessing the ability of a subject to respond to antiviral agents or to mount an immune response.

As used herein reference to "detecting" "evaluating" "enumerating" is meant in its broadest sense to include assays which qualitatively or quantitatively or semi-quantitatively test for the presence or level of a CSAP in the presence of sCSAP and hence the number of CSAP-positive cells, or, assays which qualitatively or quantitatively test for the presence or level of CSAP and sCSAP using reagents capable of distinguishing between the two forms.

Chromatographic assays are particularly sophisticated and a large number of different formats are available which are tailored to the particular reagents and instruments and the outcomes required in any particular investigation. "Rapid" assays, using chromatographic principles, are tailored for accuracy, speed and ease of use. Immunoassay or enzyme-based chromatographic assays are particularly preferred and these are described in Wild D "The Immunoassay Handbook", Nature Publishing Group, 2001 and by reference to U.S. Pat. Nos. 4,016,043; 4,590,159; 5,266,497; 4,962,023; 5,714,389; 5,877,028, 5,922,537, 6,168,956 and 6,548,309, 6,180,417, and 5,266,497 incorporated herein and information disclosed by references cited therein. Various modifications of immunochromatographic methods are described in Published US Patent Application Nos. 20010006821, 20040087036 and 20040214347 which are incorporated herein in their entirety. Immunogold filtration methods for multiple analyte analyses are described in Published US Patent Application No. 20030165970 incorporated herein.

By "detection marker" or "reporter molecule" is meant a molecule or particle which, by its chemical nature, provides an analytically identifiable signal which allows the detection of antigen bound antibody. As will be well recognised, a wide variety of different reporter systems are available and those allowing rapid visual detection are clearly the most useful in the context of point of care diagnostics.

In some embodiments, the detection marker is a colloidal particle or microparticle. Colloidal metal and metalloid particles include those comprising gold, silver, platinum, iron, copper, selenium; metal complexes such as cyclopentadienyl-manganese(I) tricarbonyl, gold cluster; and microparticles such as latex and dyed latex particles.

The present invention extends to qualitative or quantitative detection using any of the commonly used reporter molecules in this type of immunoassay such as enzymes, fluorophores or radionuclide containing molecules and chemiluminescent molecules. In the case of an enzyme immunoassay, an enzyme is conjugated to a second antibody generally by means of glutaraldehyde or periodate. Commonly used enzymes include horseradish peroxidase, glucose oxidase, beta galactosidase and alkaline phosphatase, amongst others. The substrates to be used with the specific enzymes are generally chosen for the production, upon hydrolysis by the corresponding enzyme, of a detectable colour change. Examples of suitable enzymes include alkaline phosphatase and peroxidase. It is also possible to employ fluorogenic substrates which yield a fluorescent product rather than the chromogenic substrates listed above. In all cases, the enzyme labelled antibody is added to the first antibody antigen complex, allowed to bind, and the excess reagent is washed away. A solution containing the appropriate substrate is then added to the complex of antibody-antigen antibody. The substrate will react with the enzyme linked to the second antibody, giving a qualitative visual signal, which may be further quantified, usually spectrophotometrically, to give an indication of the amount of antigen which is present in the sample. Alternatively, fluorescent compounds, such as fluorescein and rhodamine are chemically coupled to antibodies without altering their binding capacity. When activated by a illumination with light of a particular wave length, the fluorochrome labelled antibody absorbs the light energy inducing a state of excitability in the molecule followed by emission of the light at a characteristic wavelength visually detectable with a microscope.

Reference to "antibodies" includes humanized, recombinant, synthetic, hybrid and single chain antibodies. Antibodies may be conveniently prepared and used as described, for example, in Harlow and Lane, "*Antibodies: A Laboratory Manual*" (Cold Spring Harbor Laboratory, 1988). Monoclonal antibodies are conveniently prepared in pure form and in large quantities. The preparation of hybridoma cell lines for monoclonal antibody production by fusing sensitized lymphocytes with an immortal cell line and selecting specific antibody producers is routine in that art as described in Harlow and Lane (supra); and Kohler and Milstein, *European Journal of Immunology*, 6:511-519, 1976.

Methods for the construction of bacteriophage antibody display libraries and lambda phage expression libraries are well known in the art (Kang et al., *Proc. Natl. Acad. Sci. U.S.A.*, 88:4363, 1991; Clackson et al., *Nature*, 352:624, 1991; Lowman et al., *Biochemistry*, 30:10832, 1991; Burton et al., *Proc. Natl. Acad. Sci U.S.A.*, 88:10134, 1991; Hoogenboom et al., *Nucleic Acids Res.*, 19:4133, 1991, incorporated herein by reference in their entirety). One particularly advantageous approach has been the use of scFv phage-libraries (Huston et al., *Proc. Natl. Acad. Sci U.S.A.*, 85:5879-5883, 1988; Chaudhary et al., *Proc. Natl. Acad. Sci. U.S.A.*, 87:1066-1070, 1990; Clackson et al., 1991, (supra)). Various embodiments of scFv libraries displayed on bacteriophage coat proteins have been described. Further phage display approaches are also known, for example as described in International Publication Nos. WO 96/06213 and WO 92/01047 (Medical Research Council et al.) and International Publication No. WO 97/08320 (Morphosys) which are incorporated herein by reference.

Antibody single chain Fv fragments may be cloned and expressed on the surface of, for example, yeast. High affinity scFvs are selected by screening and sorting. High affinity antibodies are developed using chain shuffling strategies, that is by sequentially replacing the heavy and light chain variable (v) region genes with repertoires of v-genes from unimmunized donors. Antibodies comprising csFvs from any species may be employed.

Of particular use are display systems, which enable a nucleic acid to be linked to the polypeptide it expresses. Selection protocols for isolating desired members of large libraries are known in the art, as typified by phage display techniques. Such systems, in which diverse peptide sequences are displayed on the surface of filamentous bacteriophage, are useful for creating libraries of antibody fragments (and the nucleotide sequences that encode them) for the in vitro selection and amplification of specific antibody fragments that bind a target antigen. The nucleotide sequences encoding the $V_H$ and $V_L$ regions are linked to gene fragments which encode leader signals that direct them to the periplasmic space of *E. coli* and the resultant antibody fragments are displayed on the surface of the bacteriophage, typically as fusions to bacteriophage coat proteins (e.g., pIII or pVIII). Alternatively, antibody fragments are displayed externally on lambda phage capsids (phage bodies). An advantage of phage-based display systems is that selected library members can be amplified simply by growing the phage containing the selected library member in bacterial cells. Furthermore, since the nucleotide sequence that encode the polypeptide library member is contained on a phage or phagemid vector, sequencing, expression and subsequent genetic manipulation is relatively straightforward.

The present invention is further described by the following non-limiting Examples.

Example 1

Polyclonal and Monoclonal Antibodies to the Cytoplasmic or Extracellular Domain of CD4

Figure 3:
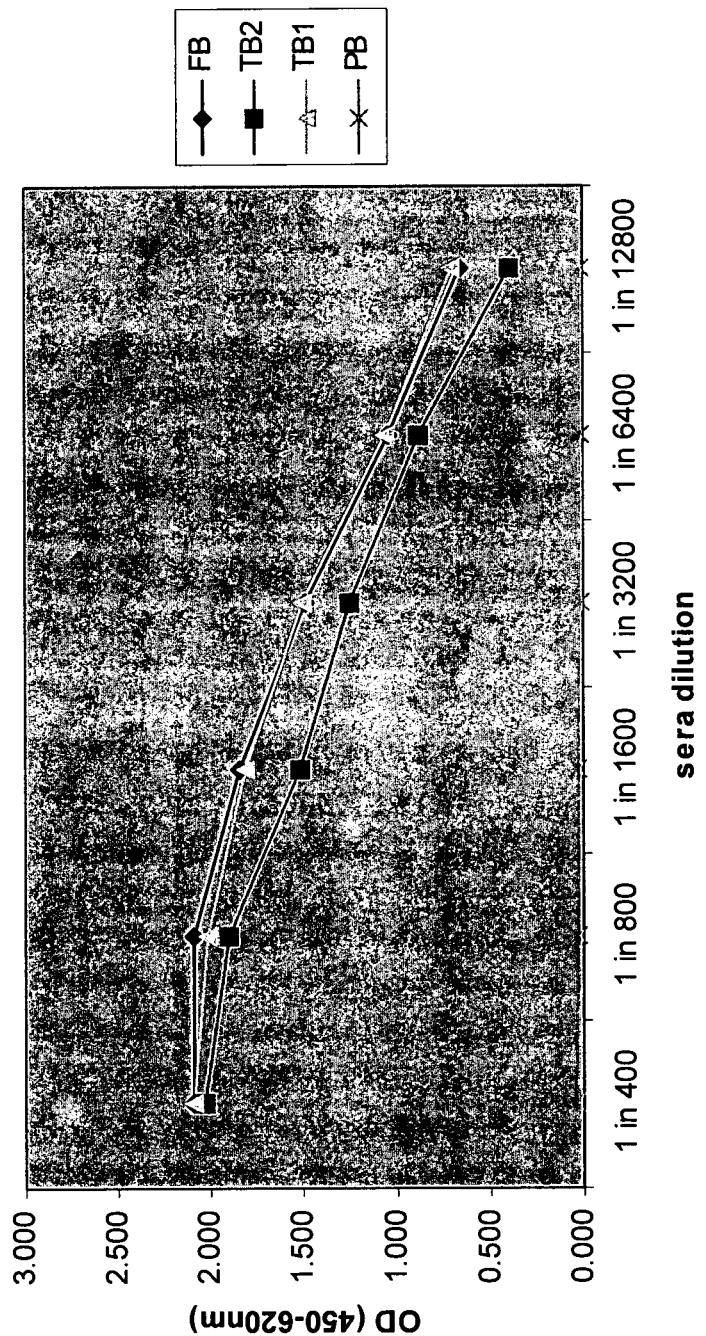
FIG. 3 is a graphical representation of the results of an ELISA assay conducted to measure the specificity and titre of sheep polyclonal antibodies to CD4 cytoplasmic peptides.
Figure 3:
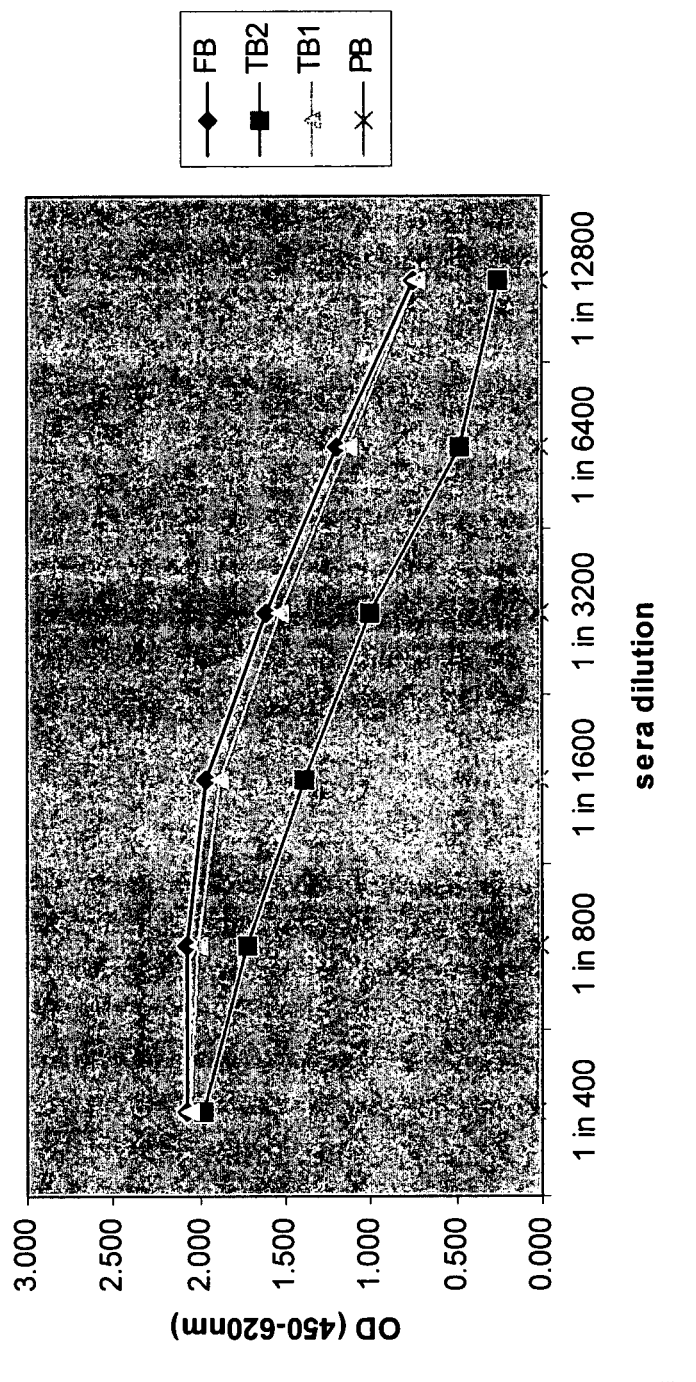
Figure 4:
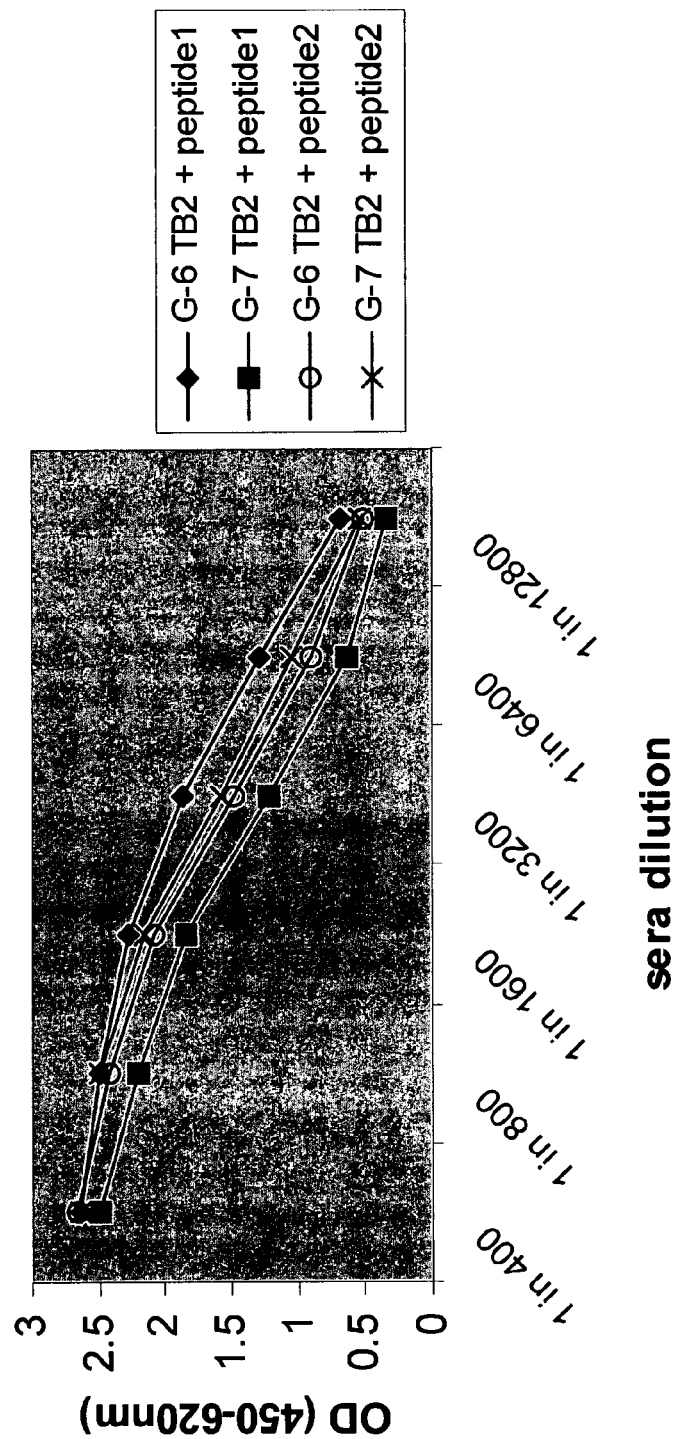
FIG. 4 is a graphical representation of the results of an ELISA assay conducted to measure the specificity of CD4 polyclonal antibodies for peptide 1 and peptide 2. As shown therein, sheep have similar reactivity to both peptides by ELISA. TB2 is blood from a second test bleed after immunisation of G-7 or G-6 sheep.
Figure 5:
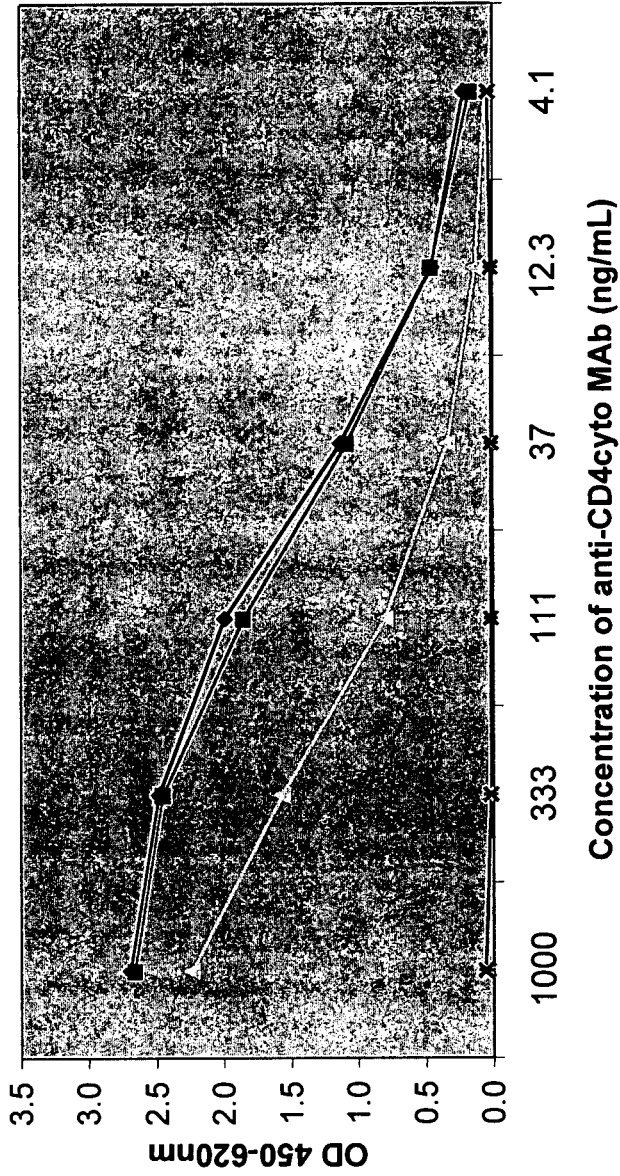
FIG. 5 is a graphical representation of the results of an ELISA assay conducted to compare the reactivity of anti-$CD4_{cyto}$ monoclonal antibodies (MAbs) to $CD4_{cyto}$ peptide 2. As shown therein, three of the monoclonal antibodies show binding to peptide 2.

Anti-CD4 polyclonal antibodies were generated in sheep against two human CD4 ectodomain subsequences P1 and P2 (SEQ ID NO: 1 and SEQ ID NO: 2). The peptide sequences and the position of the peptide in the cytoplasmic CD4 sequence are set out in FIG. 2. Two sheep, G-6 and G-7, were injected with P1 and P2 using standard procedures. The specificity and titre of polyclonal antibodies to $CD4_{cyto}$ were determined by ELISA using immobilised biotinylated peptides and detected using Streptavadin conjugated to horseradish peroxidase. The results are represented graphically in FIG. 3(A) sheep G-6 and (B) sheep G-7. Sera from either sheep recognised peptide 1 and peptide 2 equally well (see FIG. 4). Monoclonal antibodies were also generated to peptide 2 and tested by ELISA against Peptide 2 of $CD4_{cyto}$ (see FIG. 5).

Figure 6:
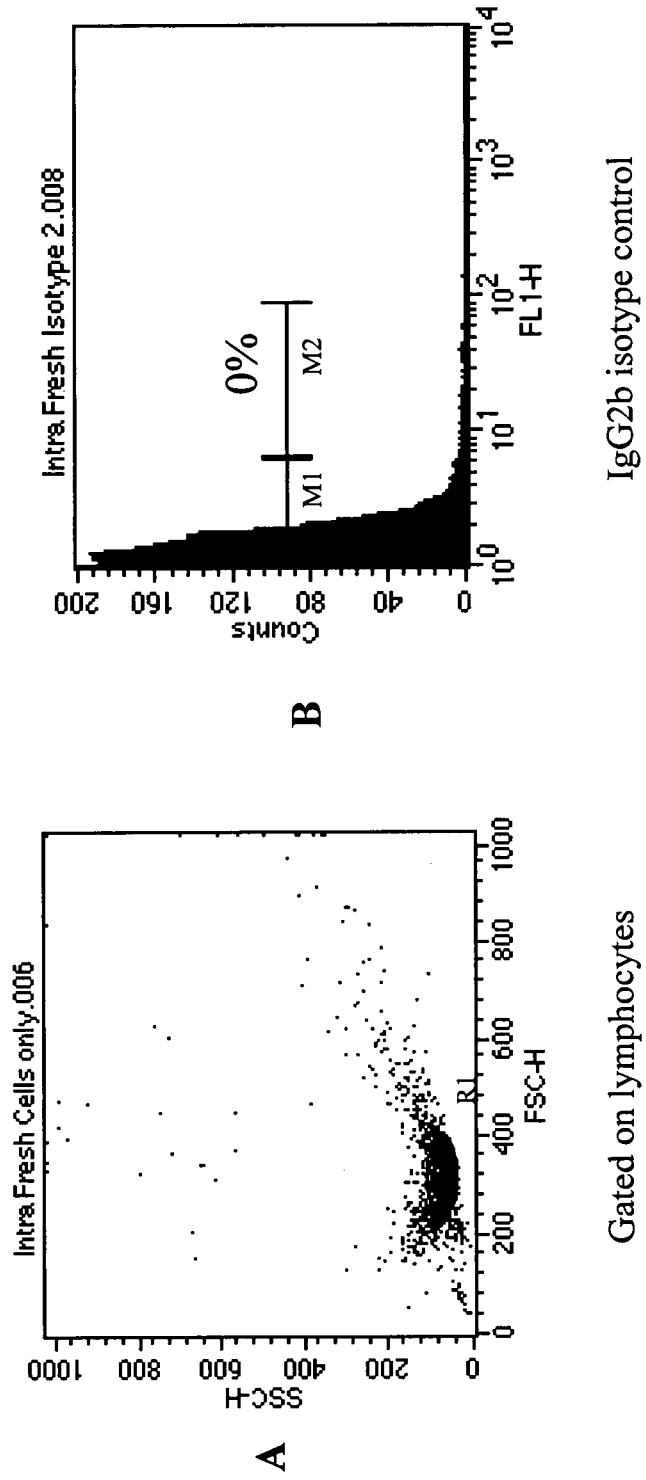
FIG. 6 is a graphical representation of the results of flow cytometry analyses conducted to assess the ability of anti $CD4_{cyto}$ monoclonal antibodies ID2 and 4B4 to bind to fresh (non-fixed/permeabilized) $CD4^+$ T-cells (A, B, C and D). Antibodies failed to bind to fresh cells.

The reactivity of monoclonal antibodies 1D2 and 4B4 were tested in immunofluorescence assays on HeLa cells and JC53 T-cells. Both monoclonal antibodies (at 10 micrograms per ml) showed no reactivity against HeLa cells. However, the antibodies recognised intracellular components on fixed T-cells. SIM2 monoclonal antibody recognising the ectodomain of CD4 did not recognise HeLa cells but showed binding to the surface of JC53 cells at 10 micrograms per ml. As expected, monoclonal antibodies 1D2 and 4B4 failed to bind to fresh CD4 positive T-cells (FIG. 6). In contrast, permeablised cells were detected by both monoclonal antibody 1D2 and 4B4 (See FIGS. 7C and D).

Antibodies or antigen binding fragments may be generated against CD4 molecules from different species. In an illustrative example the sequences of cytoplasmic domains from mouse, rabbit, chicken, sheep are provided below.

```
human CD4:    421rcrhrrrqae rmsqikrlls ekktcqcphr fqktcspi458 mouse CD4:    420rcrh[qq]rq[a] rmsqikrlls ekktcqcphr [m]q[shnl]i457 rabbit CD4:   42[k]crhr[h]qaq rmsqi[k]lls ekktcqcphr [h]kt[ynl]l459 chicken CD4:  455[wqr]r[kr]ar rm[a][a]k[qyl][l] ekktcqc[qr]r [my]k487 sheep CD4:    418[kw]hrrrqae rmsqikrlls ekktcqcphr [h]kt[hk]lt455
```

Boxed residues highlight the differences between human CD4 and the species CD4.
key: human & mouse (are ~79% conserved sequences 30/38)
human & rabbit (are ~76% conserved sequences 29/38)
human & chicken (are ~55% conserved sequences 18/33)
human & sheep (are ~84% conserved sequences 32/38)
NB.
The sequence 'ekktcqc' is the putative $p56^{lck}$ binding site, conserved in all species.

Example 2

CD4 ELISA

A CD4 capture ELISA was developed to allow quantification of cell associated CD4 without interference from soluble CD4, lacking a cytoplasmic domain. Antibodies directed against the cytoplasmic domain of CD4 are used as "capture" antibodies in combination with antibodies directed against the extracellular domain of CD4 as "detection" antibodies. Only cell-associated CD4 is measured while soluble CD4 lacking the cytoplasmic domain or the epitope recognised by anti-CD4 cyto antibodies is excluded. The CD4 capture ELISA shows close correlation with flow cytometry and has been adapted to provide a rapid point of care diagnostic test as shown herein.

Figure 2:
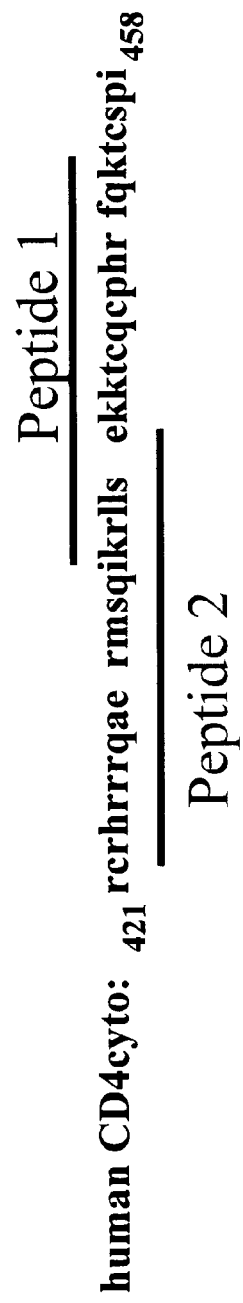
FIG. 2 is a diagrammatic representation of the human CD4 cytoplasmic domain and the sequence of sub sequence peptides that were synthesised in order to generate antibodies against the cytoplasmic domain. Peptide 1 comprises 17 amino acids from amino acids 436 to 454 with amino acids 446 to 447 (QC) omitted (SEQ ID NO: 1). Peptide 2 comprises 20 amino from amino acids 422 to 441 of human CD4 (SEQ ID NO: 2). Numbering of amino acids is as described in Example 1.
Figure 9:
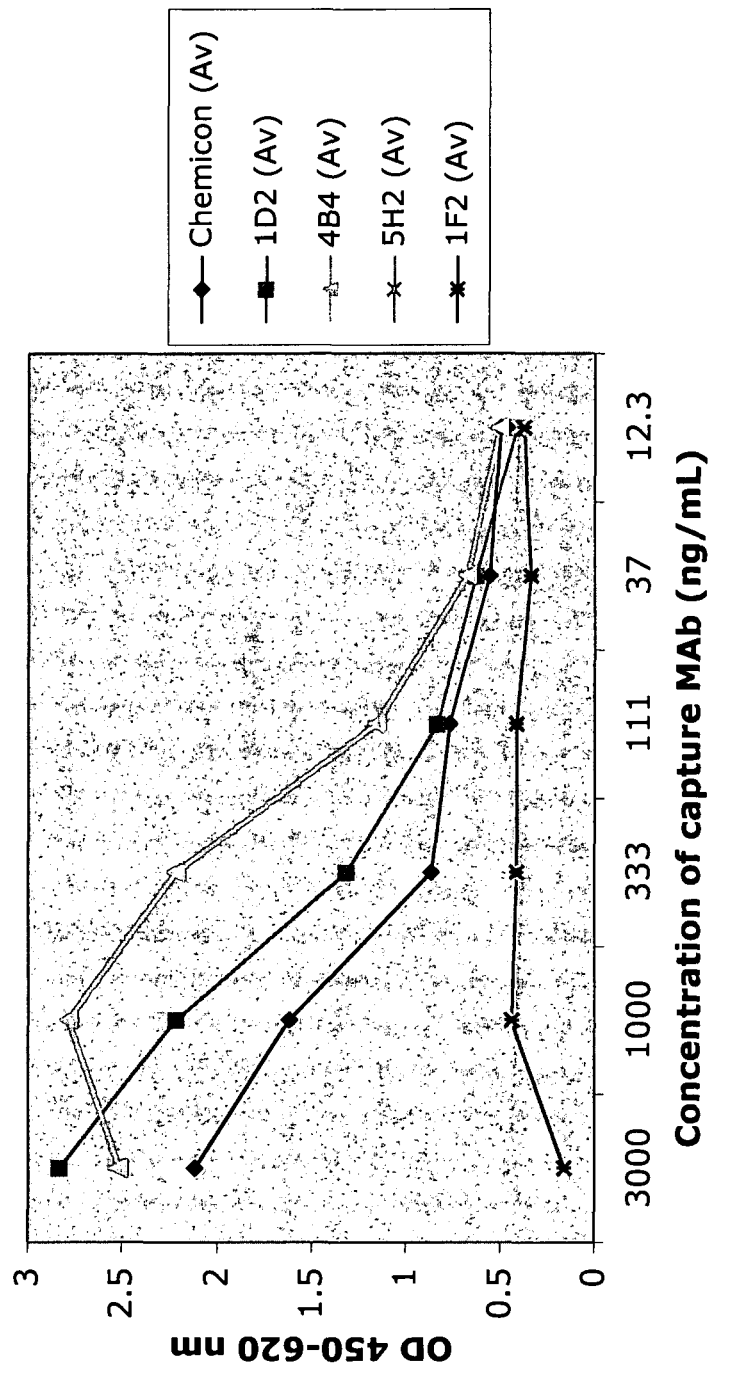
FIG. 9 is a graphical representation of results of an ELISA conducted to measure the reactivity of monoclonal antibodies directed to the cytoplasmic domain of CD4 including a commercially available anti-CD4 cyto monoclonal antibody (chemicon).

FIG. 9 shows the results of an ELISA conducted to measure the reactivity of monoclonal antibodies directed to the cytoplasmic domain of CD4 including a commercially available anti-CD4 monoclonal antibody (Chemicon). Antibodies were generated against Peptide 1 (SEQ ID NO: 1) and Peptide 2 (SEQ ID NO: 2) as shown in FIG. 2.

Figure 10:
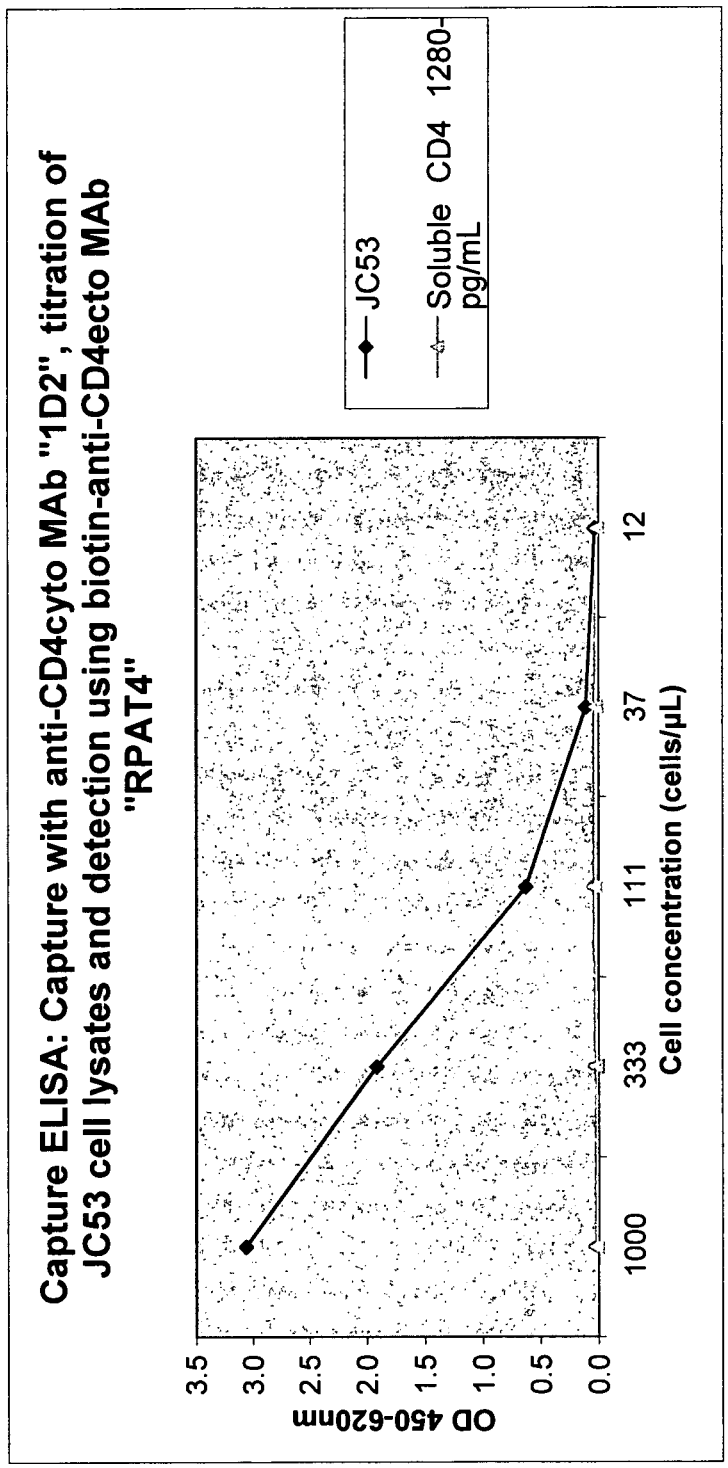
FIG. 10 is a graphical representation of results of a capture ELISA conducted to measure the specificity of monoclonal antibody 1D2 directed to the cytoplasmic domain of CD4 and its ability to capture CD4 from JC53 cell lysates and detection with a monoclonal antibody directed to the ectodomain of CD4 (RPAT4). 1D2 captured CD4 from JC53 cell lysates that was detectable with RPAT4, but soluble CD4 was not captured.

FIG. 10 shows the results of a capture ELISA conducted to measure the specificity of monoclonal antibody ID2 directed to the cytoplasmic domain of CD4 and ability to capture CD4 from JC53 cell lysates and detection with a monoclonal antibody directed to the ecto domain of CD4 (RPAT4).

Figure 11:
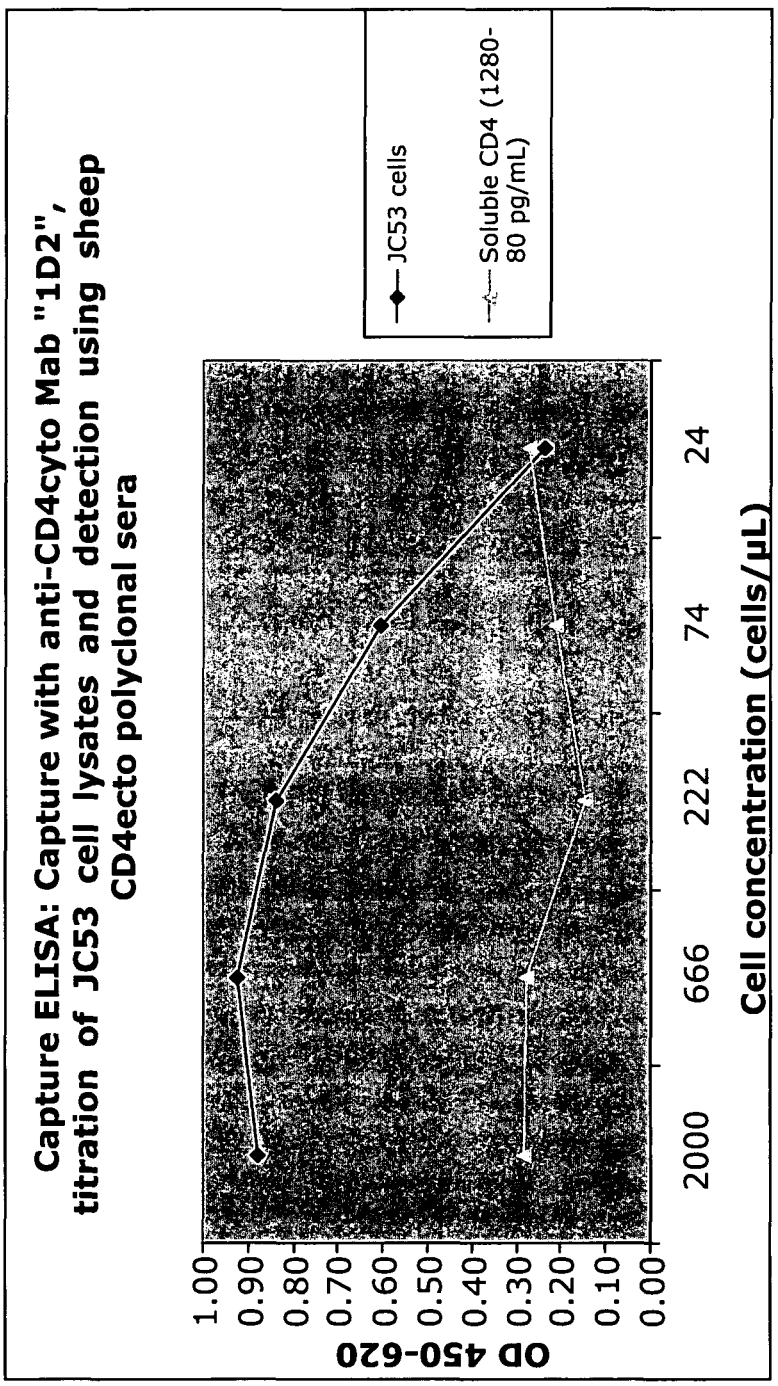
FIG. 11 is a graphical representation of results of a capture ELISA conducted to measure the specificity of monoclonal antibody 1D2 directed to the cytoplasmic domain of CD4 and its ability to capture CD4 from JC53 cell lysates and detection with a polyclonal antibody directed to the ecto domain of CD4. 1D2 captured CD4 from JC53 cell lysates that was detectable with polyclonal antibody to the CD4 ectodomain, but soluble CD4 was not captured.

FIG. 11 shows the results of a capture ELISA conducted to measure the specificity of monoclonal antibody ID2 directed to the cytoplasmic domain of CD4 and ability to capture CD4 from JC53 cell lysates and detection with a polyclonal antibody directed to the ecto domain of CD4.

Figure 12:
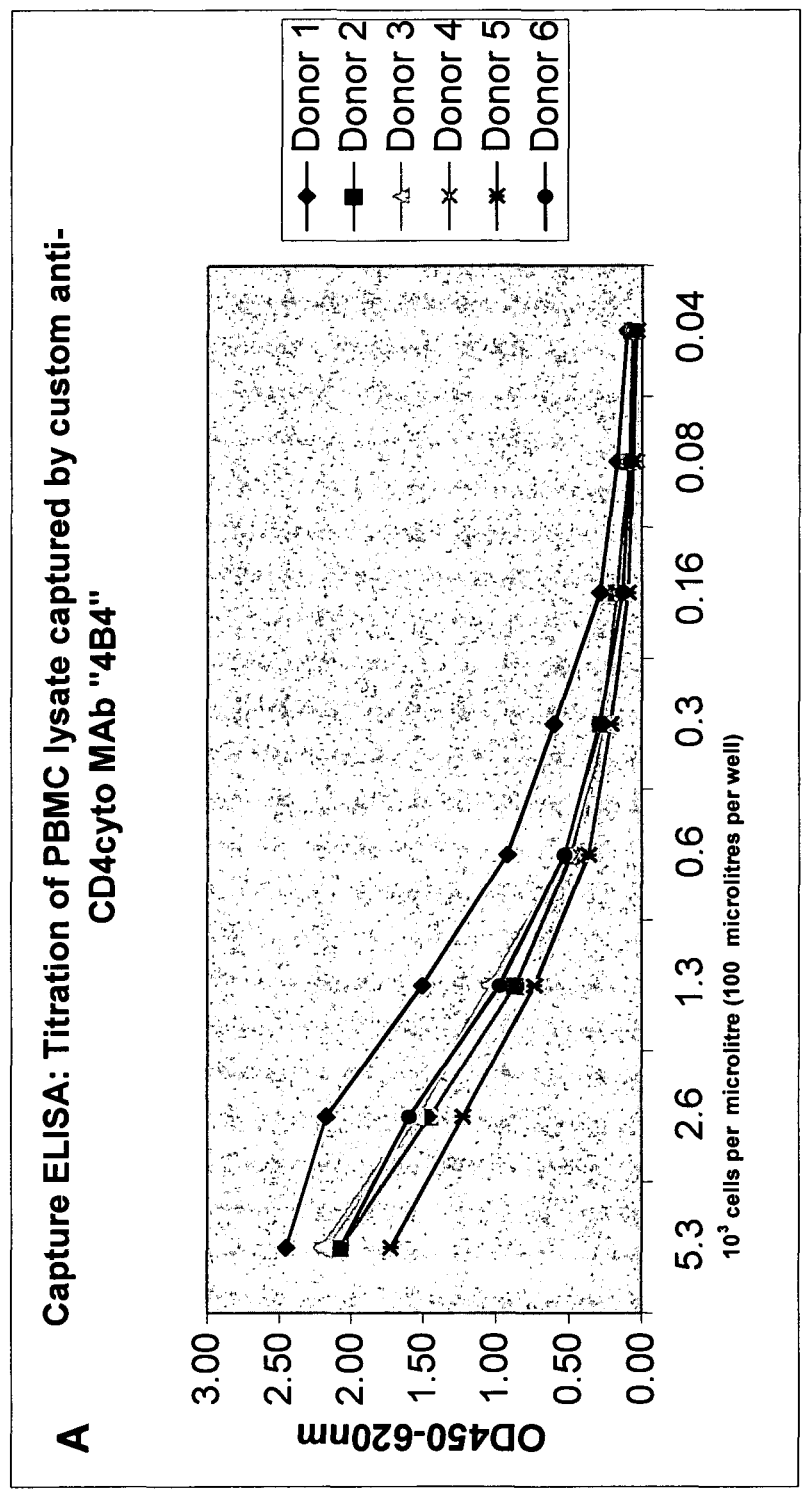
FIG. 12 is a graphical representation of results of capture ELISAs of cellular CD4 from donor peripheral blood mononuclear cell (PBMC). A shows a titration of PBMC lysate captured by monoclonal antibody 4B4 from Donors 1 to 6, who have different proportions of CD4 T-cells in the total PBMC population. B shows the capture of cellular CD4-enriched lymphocytes.
Figure 12:
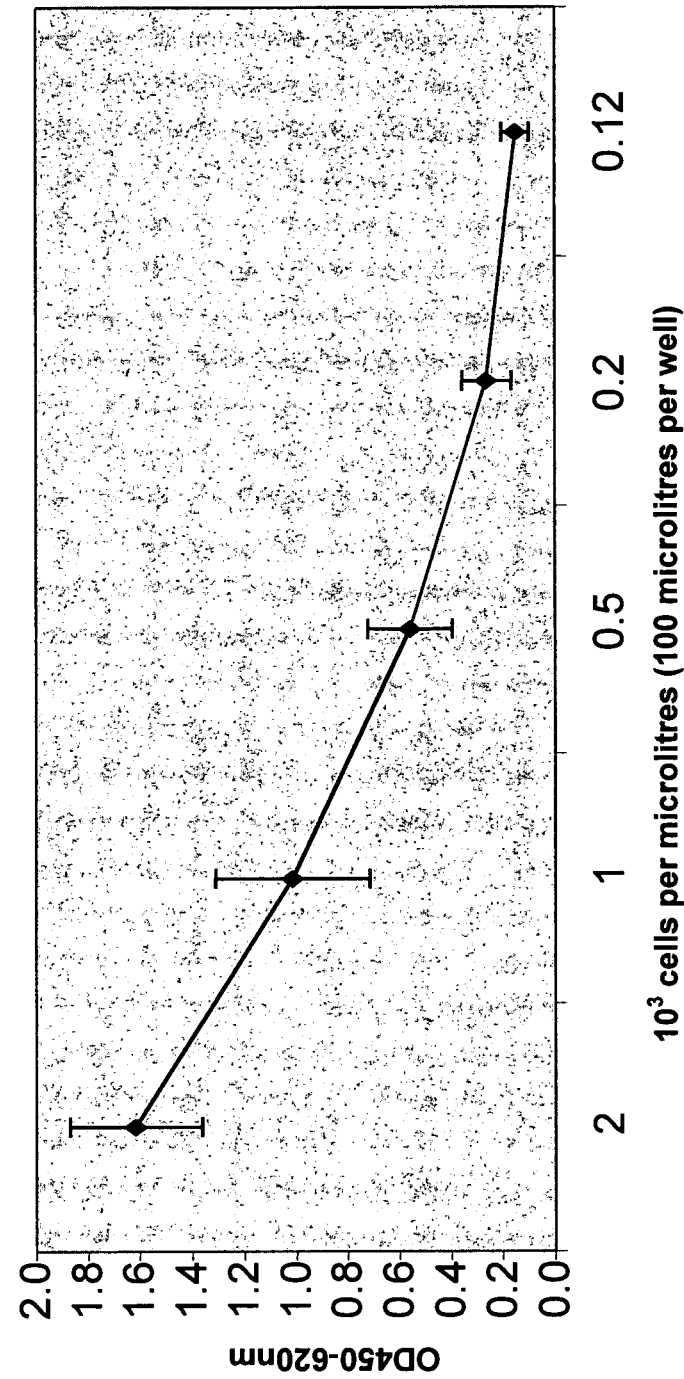

FIG. 12 shows the results of capture ELISAs of cellular CD4 from donor peripheral blood mononuclear cell (PBMC). A) shows a titration of PBMC lysate captured by monoclonal antibody 4B4 from Donors 1 to 6. B) shows the capture of cellular CD4-enriched lymphocytes.

In an illustrative embodiment, the ELISA protocol a standard amount of CD4 comprising cytoplasmic and extracellular domains is used as a control diluted in PBS+0.5% Tween20. Whole blood or diluted blood is added to an equal volume of lysis buffer comprising 10% Triton-X100 lysis buffer and dispensed into designated wells of a standard ELISA plate coated with anti-CD4 cyto antibody. The ELISA plate is sealed and incubated at room temperature (18 to 23° C.) for 60 minutes. Biotinylated anti-CD4 monoclonal antibody directed to the ectodomain of CD4 is diluted in 0.05% Tween20 to give a final concentration of 0.25 micrograms per ml. ELISA plates are washed with standard ELISA wash buffer and drained and 100 microlitres of diluted anti-CD4 biotinylated monoclonal antibody is added to each well. The plates are sealed and incubated at room temperature for 60 minutes. Thereafter, the plates are washed (times 6) using ELISA wash buffer and drained. Strepdavidin-horseradish peroxidase conjugate is diluted in 1:1000 in PBS 0.05% Tween20 and 100 microlitre added to each well. ELISA plates are sealed and incubated at room temperature for 60 minutes. Thereafter the plates are washed and drained as before prior to addition of enzyme chromogen substrate tetramethylbenzidine (TMB) diluted in substrate buffer according to the manufacturer's instructions. The enzyme reaction is allowed to proceed for approximately 15 minutes in the dark at room temperature and at the end of the substrate incubation period 100 microlitres of stock solution is added to each well prior to reading plates for optical density using a dual λ ELISA reader with a 450 millimetre filter and a 620 millimetre filter as a reference. The mean standard deviation and % CV is calculated and a mean OD readings generated using a scatter plot.

Example 3

Capture ELISA Assays Show Correlation Between OD and Number of CD4+ T-Cells

Figure 13:
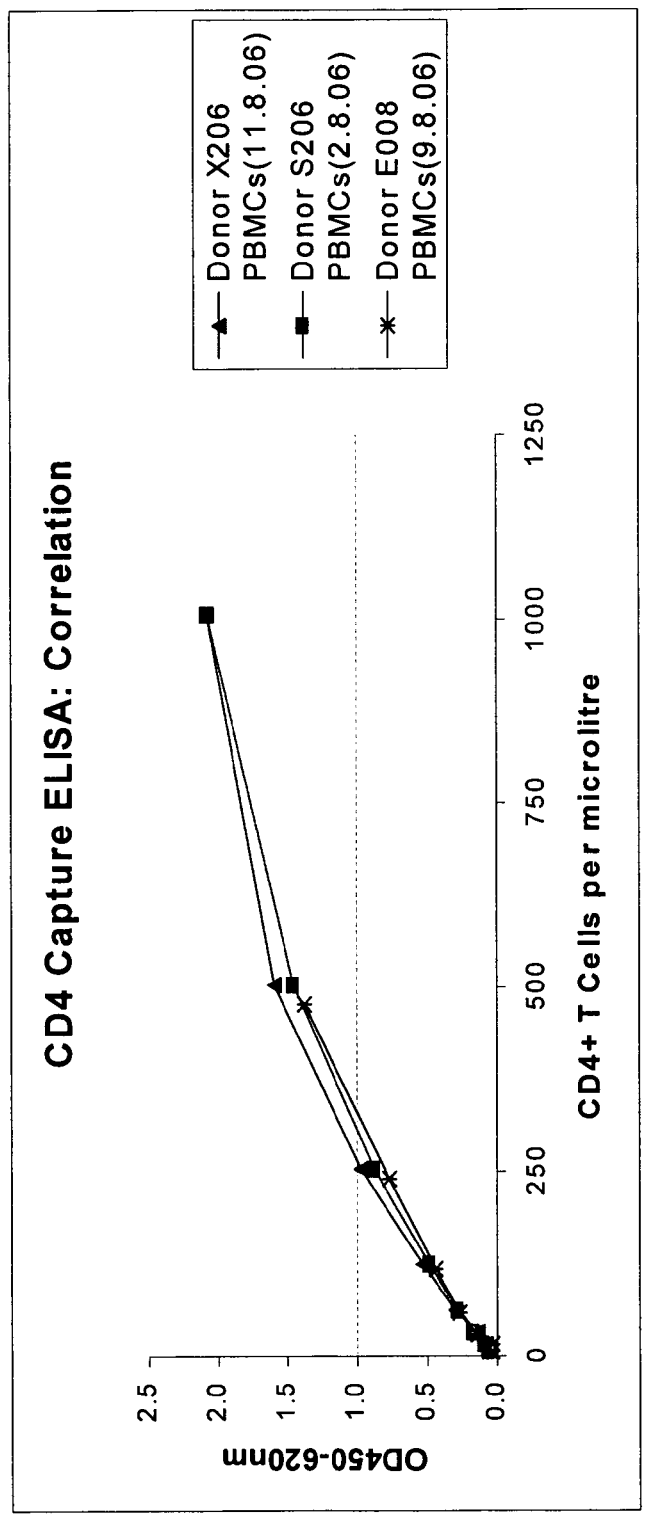
FIG. 13 is a graphical representation of results of capture ELISAs of cellular CD4 from donor peripheral blood mononuclear cell (PBMC). The results from three donors are shown and a correlation between OD450-620 and the number of CD4+ T-cells per microlitre.
Figure 14:
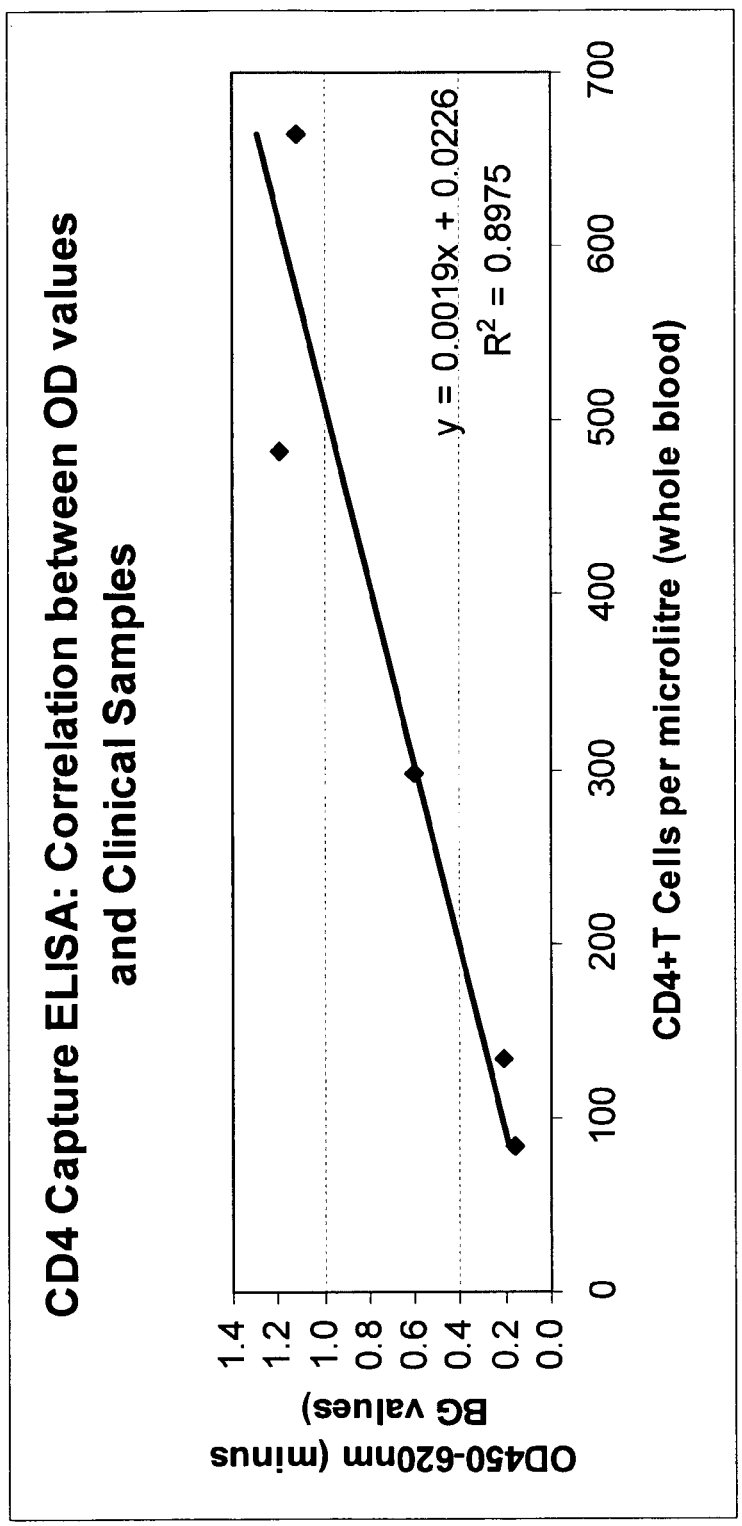
FIG. 14 is a graphical representation of results of capture ELISAs of cellular CD4 from donor peripheral blood mononuclear cell (PBMC). The results from 5 different HIV-infected patients are shown and demonstrate a close correlation between OD450-620 and the number of CD4+ T-cells per microlitre of whole blood.

ELISAs of cellular CD4 from donor peripheral blood mononuclear cell (PBMC) were conducted and the results show in FIGS. 13 and FIG. 14. The results from three donors are shown on FIG. 13 and a correlation between OD450-620 and the number of CD4+ T-cells per microlitre. The results from clinical samples from 5 separate HIV-infected patients are shown in FIG. 14 and a positive correlation between OD450-620 and the number of CD4+ T-cells per microlitre of whole blood is demonstrated.

Example 4

Immunochromatographic Devices Employing Antibodies to the Cytoplasmic Domain of a CSAP in Accordance with the Present Invention Immunochromatography or immunographic devices provide a robust technology that is used in a wide variety of rapid, point of care diagnostic tests manufactured by many different companies throughout the world. This provides redundancy in manufacturing capability and ready acceptance of the technology in target countries. Immunochromatographic devices have been used having as a test platform for measurement of cell-associated CD4 as a correlate of CD4 T-cell numbers. Soluble CD4 (comprising an extracellular domain but no cytoplasmic domain (present in blood)) is excluded in these assays. In addition, in some embodiments, CD4 expressed on monocytes is excluded in subject assays. In some embodiments, an immunochromatographic device provides a quantitative estimate of CD4 T-cell numbers, (less than 250, more than 250, 250 to 350, 350 to 500, 250 to 500 and more than 500 cells per microlitre) by visual comparison with standards in each test strip. This fulfils the current criteria for access of adult patients to anti-retroviral drugs. A further test, having appropriate means for detecting appropriate cells numbers, is made using the same methods for monitoring pediatric HIV patients who have, on average, higher levels of CD4 T-cell counts (i.e., less than 500, 500 to 1000 and 1000 to 2000 cells per microlitre).

Figure 15A:
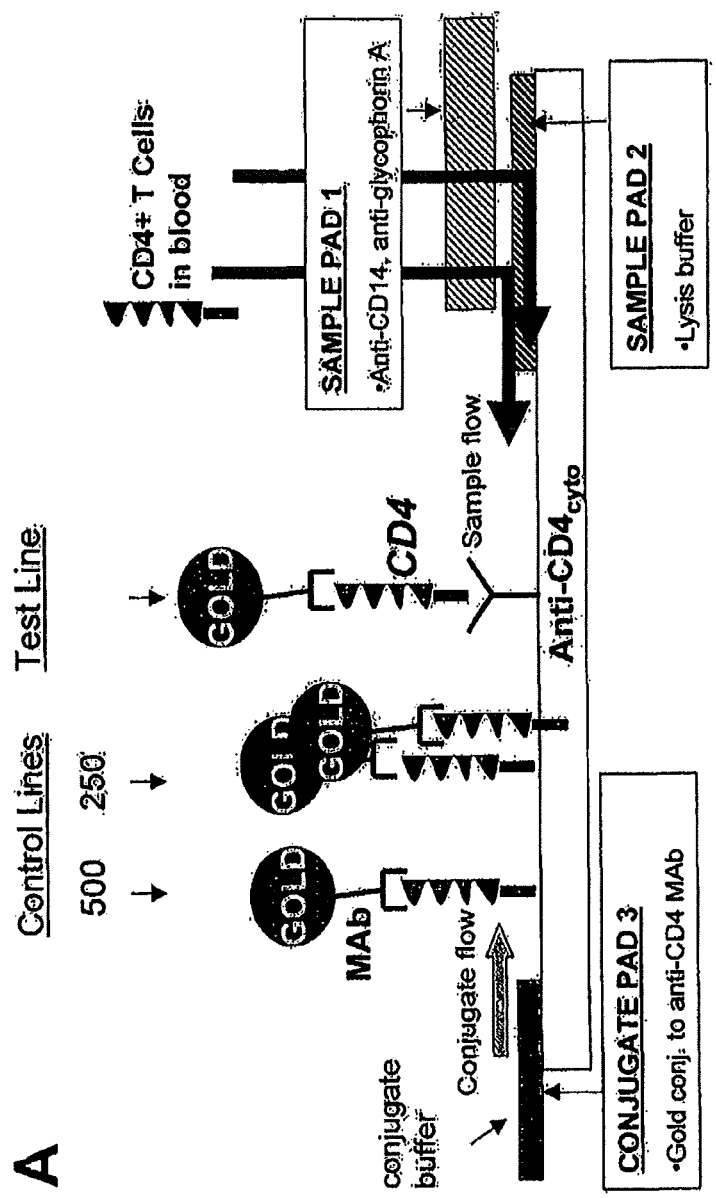
FIG. 15 (A) is a schematic representation of the design for an immunochromatographic device for detection of full length cell-associated CD4 and estimation of CD4+ cell numbers thereby.
Figure 15B:
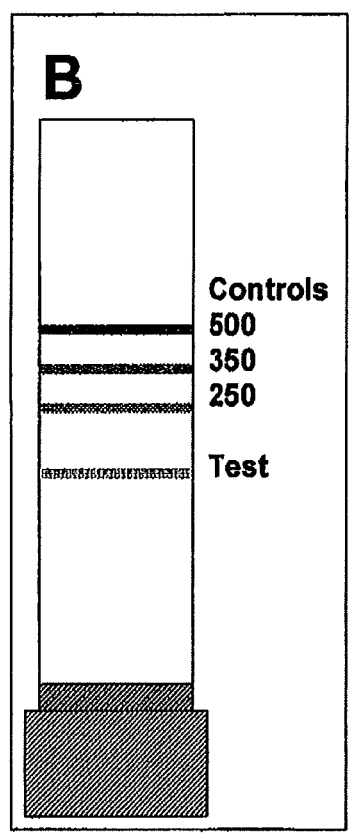

In FIG. 15 an immunochromatographic device for detection of full length cell-associated CD4 and estimation of $CD4^+$ cell numbers thereby is schematically described. A porous membrane (such as nitrocellulose) is prepared by striping a test line consisting of monoclonal antibody to the cytoplasmic domain of human CD4, a control line consisting of anti-mouse IgG (or other controls), and an inert limit line to provide a guide during assay performance. The nitrocellulose is assembled together with a "sample pad" (sample portion) at one end, consisting of porous material to which has been applied a defined quantity of blood and to which reagents may have been added to trap red blood cells or monocytes and other extraneous material in the sample, a second sample pad (lysis portion) comprising lysis buffer, and a "conjugate pad" (conjugate portion) at the other end, consisting of porous material, to which is applied the conjugate (detection marker) consisting of a detection reagent (such as colloidal gold) conjugated to anti-CD4 antibody" and an absorbent material (sucker portion).

In some embodiments, the lysis step is optional in certain circumstances such as when, for example, an antibody or other agent capable is employed that is capable of penetrating a cell or where a subject is ill and the majority of a particular cell type are, in any event, permeable to passage of anti-CSAP agents.

Example 5

Cloning and Expression of Full-Length CD4 and Recombinant Soluble Full-Length CD4 Lacking a Transmembrane Domain(TM^CD4)

The ELISA and rapid point of care tests for CD4 are required to give a quantitative or semi-quantitative measure of the total amount of the cell associated and/or soluble/extracellular CD4 present in a sample, providing an estimate of the number of CD4 T-cells. For this purpose, it is useful to have a defined source of CD4 that can be used in quality control and as an assay standard. Human T-cells or cells transformed with full-length human CD4 can be used as a source of CD4, but may give inconsistent yields and require extensive purification of the membrane-bound CD4 molecule. The inventors reasoned that a recombinant form of CD4 that was released from cells as a soluble form, while retaining the cytoplasmic domain that is required for reactivity in the CD4 capture ELISA, would be more suitable for this purpose. It is known in the art that deletion of the transmembrane domain of a protein can result in secretion of the fused ectodomain-cytoplasmic domain protein. A version of CD4 with deletion of the transmembrane domain, designated TM^CD4, was therefore produced. The structure of one embodiment of the protein is shown schematically in FIG. 1.

The CD4 sequence was obtained from the T4pmV7 plasmid obtained from NIH AIDS research and reference program Cat No 158. In order to make the soluble TM^CD4 form of CD4 the primers were designed so they produced two individual PCR products. The first product used primers RL1 and RL3 resulting in a 1.2 kb band which has an EcoR1 restriction site at the 5' end of the extracellular domain and some overlapping sequence corresponding to the cytoplasmic tail at the 3' end. The second PCR product used primers RL2 and RL4 resulting in a 120 bp band that has some overlapping extracellular domain sequence at the 5' end of the cytoplasmic tail and a XbaI restriction site at the 3' end. To make the final PCR product the 2 PCR products were then used as the template for a third PCR reaction and primers RL1 and RL2 are used. A full length CD4 construct was generated using primers RL1 and RL2 with plasmid T4pmV7 in a standard PCR reaction.

```
Primers:
RL1
                                         SEQ ID NO: 3
5' CGG GAA TTC ACA ATG AAC CGG GGA GTC CC (sense)

RL2
                                         SEQ ID NO: 4
5' GGC TCT AGA TCA AAT GGG GCT ACA TGT CTT C
(antisense)

RL3
                                         SEQ ID NO: 5
5' G CCT TCG GTG CCG GCA CCT CTG CAC CGG GGT GGA CC
(antisense)

RL4
                                         SEQ ID NO: 6
5' GG TCC ACC CCG GTG CAG AGG TGC CGG CAC CGA AGG C
(sense)
```

The restriction site EcoR1 in primer RL1 and the restriction site XbaI in primer RL2 are highlighted in bold and underlined. The extracellular region in both the primers RL3 and RL4 are highlighted in bold and italics and the cytoplasmic tail is normal text.

Both the full length CD4 construct (FLCD4) and the soluble CD4 construct with a cytoplasmic domain without the TM region (CD4^TM) were cloned into the EcoR1 and XbaI restriction sites of pcDNA4/HisMax version C (Invitrogen).

Clones were identified by restriction digests and sequencing. The full nucleotide and amino acid sequence of the insert and encoded protein for TM^CD4 is shown in FIG. 16 (SEQ ID NO: 7) and FIG. 17 (SEQ ID NO:8) respectively. Variants of the recited sequences are contemplated, such as, for example those derived from different naturally occurring sequences or from modification of one or up to 20 nucleotide or amino acid modifications. Modifications that result in conservative amino acid changes are preferred in some embodiments and these are as set out in Tables 2 and 3.

Example 6

Detection of TM^CD4 in CD4 Capture ELISA and Western Immunoblotting

Figure 18:
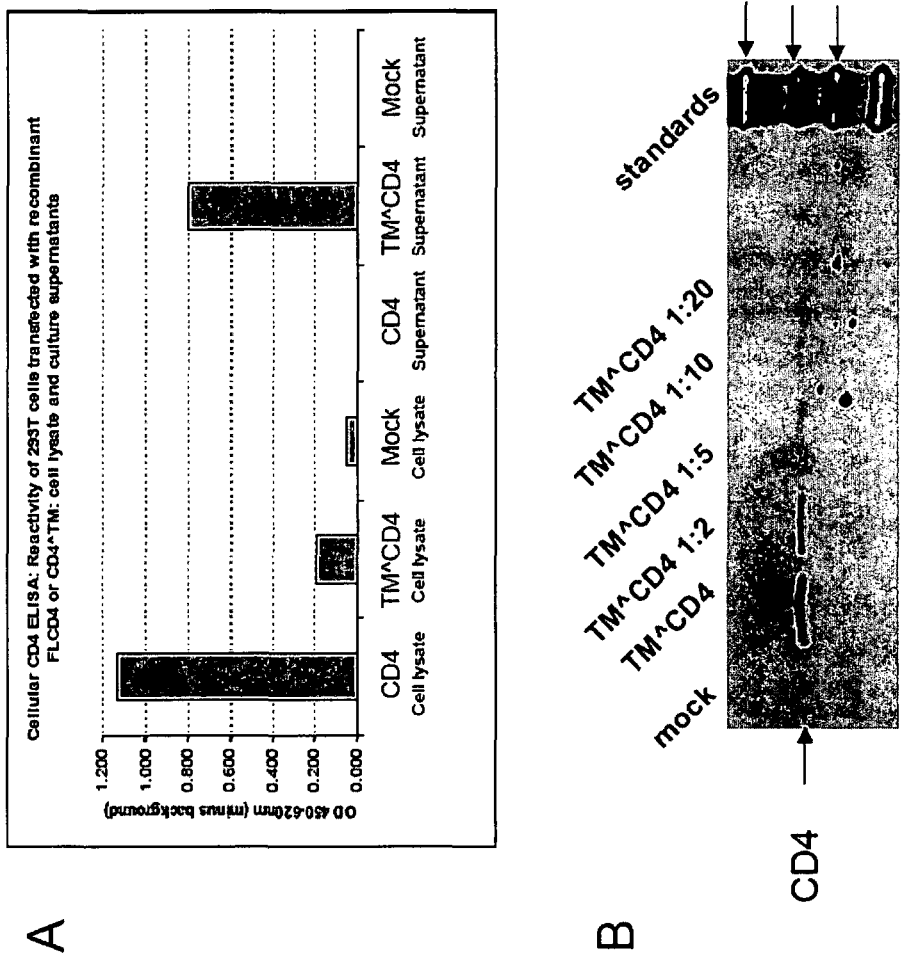
FIG. 18 is a graphical and photographic representation of data showing the detection of recombinant TM^CD4 by ELISA (A) and by Western immunoblotting (B). (A) Full-length (FL) CD4 or TM^CD4 were expressed in 293 T-cells by transfection of the respective pcDNA4/HisMax constructs, or mock-transfected. Cell lysates and cell supernatants were tested by CD4 ELISA using the method described. The results show that full-length CD4 is efficiently expressed in cells but is not released into the supernatant, whereas TM^CD4 is efficiently expressed in cells and most of the recombinant protein is released into the supernatant, allowing easy purification if required. (B) TM^CD4 was detected in culture supernatant by Western immunoblotting with custom MAb 4B4 (3 µg/ml) against the cytoplasmic domain of CD4.

Recombinant TM^CD4 was detected by ELISA and by Western immunoblotting (see FIG. 18). Full-length CD4 or TM^CD4 were expressed in 293 T-cells by transfection of the respective pcDNA4/HisMax constructs, or mock-transfected, and cell lysates and cell supernatants were tested by CD4 ELISA, using the method described. The results (see FIG. 18A) show that full-length CD4 is efficiently expressed in cells but is not released into the supernatant, whereas TM^CD4 is efficiently expressed in cells and most of the recombinant protein is released into the supernatant, allowing easy purification if required. TM^CD4 was detected in culture supernatant by Western immunoblotting with custom MAb 4B4 (3 µg/ml) against the cytoplasmic domain of CD4 (see FIG. 18B).

Example 7

TM^CD4 as Control Reagent in ELISA and Rapid, Point of Care Assays

Supernatant from HEK293 cells stably transfected with the TM^CD4 plasmid were serially diluted (starting at 1:5 dilution) for assay by ELISA (A) (see FIG. 19), showing a linear response in the ELISA demonstrating the utility of the TM^CD4 as a control reagent for estimating total CD4 T-cell numbers in the CD4 ELISA assay. For example, four different samples of whole blood were tested in the same assay (samples IDS72, 51, 40, 49), and the relative amount of CD4 compared to the standard can be estimated using the regression curve shown (in red), or other methods. To enable conversion of the amount of CD4 to the number of CD4 T-cells per microlitre, a reference sample of whole blood was tested multiple times by Flow cytometry and ELISA in comparison with the TM^CD4 standard, allowing the correct conversion factor to be determined (data not shown). As shown in FIG. 19B, supernatant from two different stable HEK293-TM^CD4 cell line clones (H5 and F5) were detected by immunochromatographic rapid point of care assay, showing that TM^CD4 can also be used as a positive control reagent or standard in such assays. In some embodiments, TM^CD4 is used as an antigen for the production of Ab.

Example 8

Figure 20:
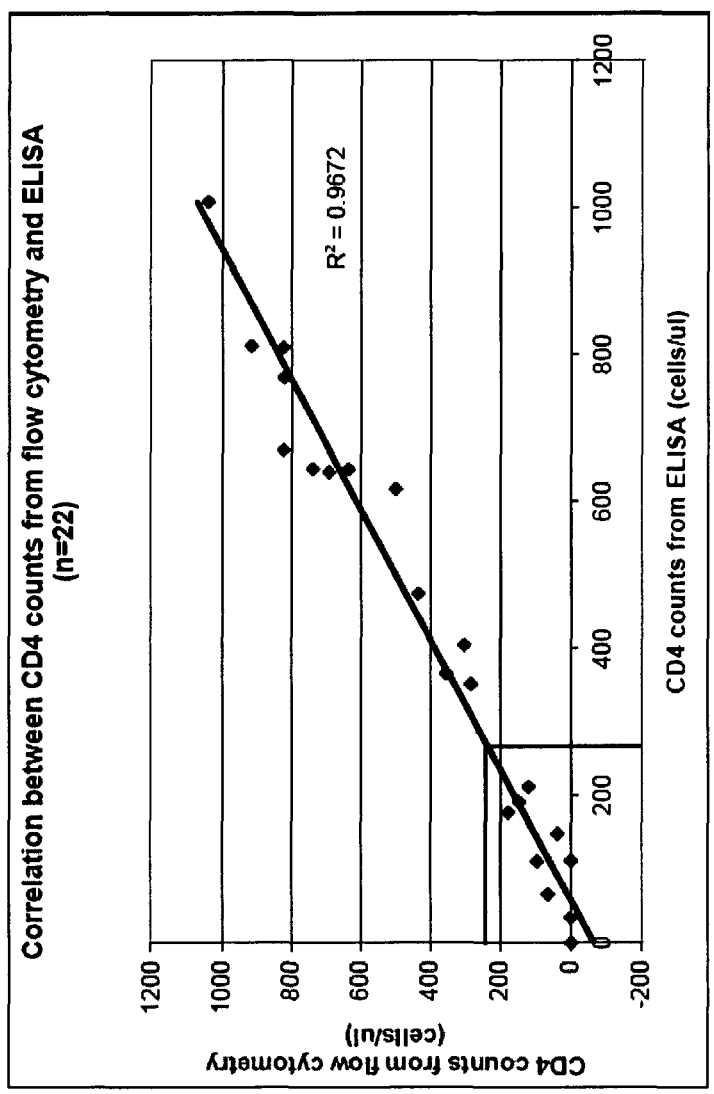
FIG. 20 is a graphical representation showing the good correlation between CD4 cell numbers calculated by flow cytometry and ELISA. Using the recombinant soluble form of CD4 as an internal assay control for the CD4 ELISA, and conversion factor based on parallel determination of a reference sample by flow cytometry and ELISA, very close correlation is obtained for the estimated CD4 T-cell numbers using CD4 ELISA compared to CD4 flow cytometry. In particular, note that all samples are correctly identified as being either greater than, or less than, 250 T-cells per microlitre, as shown in the boxed region. In this assay, monocytes were removed from whole blood using CD14 magnetic beads before assay of whole blood for CD4 T-cells by ELISA.

Strong Correlation in Estimates of CD4 T-Cell Counts Between CD4 Capture ELISA Using TM^CD4 as Standard, and Flow Cytometry Using the recombinant TM^CD4 as an internal assay control for the CD4 ELISA, and a conversion factor based on parallel determination of a reference sample by Flow cytometry and ELISA, a very close correlation is obtained for the estimated CD4 T-cell numbers using CD4 ELISA compared to CD4 flow cytometry. As shown in FIG. 20, all samples are correctly identified as being either greater than, or less than, 250 T-cells per microlitre, as shown in the boxed region. In this assay, monocytes were removed from whole blood using CD14 magnetic beads (Dynabeads CD14 (Dynal Biotech Cat No 111.49)) before assay of whole blood for CD4 T-cells by ELISA. Accurate counts can generally be obtained without monocyte removal.

Example 9

Figure 21:
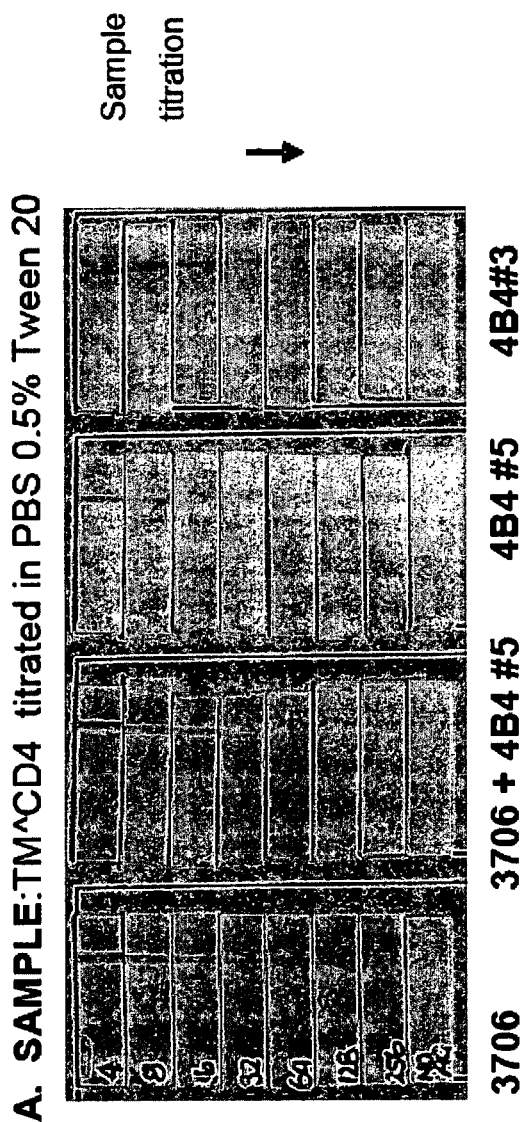
FIG. 21 is a photographic representation of results in the rapid immunochromatographic format showing a good correlation between different amounts of TM^CD4 (as a surrogate for CD4 comprising a cytoplasmic domain) and signal strength. This demonstrates that the TM^CD4 is useful as a control reagent for preparation, testing and quality control of both ELISA and rapid, point of care formats of CD4 assays. This Figure also demonstrates that both the Chemicon 3706 anti-cytoplasmic domain Mab, and the custom 4B4 anti-cytoplasmic domain Mab, can be used separately or as a mixture for capture of CD4 in the rapid format of the test. Further, this demonstrates that the signal strength in the rapid format is proportional to the amount of CD4 in the sample, allowing the use of the rapid point of care format for quantitative or semi-quantitative estimation of CD4 T-cell numbers.

Correlation Between Amount of CD4 (TM^CD4) and Signal Strength in Rapid, Point of Care Assay Using the recombinant TM^CD4 a clear dose-response curve can be seen (see FIG. 21) for signal intensity in the rapid format compared to the amount of TM^CD4 in the assay. This demonstrates that the TM^CD4 is useful as a control reagent for preparation, testing and quality control of both ELISA and rapid, point of care formats of CD4 assays. This Example also demonstrates that both the Chemicon 3706 anti-cytoplasmic domain Mab, and the custom 4B4 anti-cytoplasmic domain Mab, can be used separately or as a mixture for capture of cyto CD4 in the rapid format of the test. Further, this demonstrates that the signal strength in the rapid format is proportional to the amount of cell-associated CD4 in the sample, allowing the use of the rapid point of care format for quantitative or semi-quantitative estimation of CD4 T-cell numbers.

Example 10

Correlation Between Number of CD4 T-Cells and Signal Strength in Rapid, Point of Care Assay Actual test results for rapid point of care assay format, using purified T-cells at the indicated numbers of cells per microlitre (reacting at Test lines) (see FIG. 22A). Control lines were prepared to be equivalent to 500 T-cells/microlitre and 250 T-cells/microlitre, by striping biotinylated monoclonal antibody that reacts directly with the anti-biotin gold conjugate. It can be seen (see FIG. 22B) that visual discrimination allows the level of CD4 T-cells in the sample to be correctly identified as more than or less than 250 cells per microlitre or more than or less than 500 cells per microlitre. Test was performed on Millipore HFP90 nitrocellulose membrane with Chemicon MAb 3706 (test line capture) striped at 0.5 mg/mL; SAMPLE: 50 µl CD4+ve T cells in 1% Tx100/PBS; DETECTION: 13B8.2-biotin/anti-biotin gold. It is obvious that any reactive protein could be used as the control lines, such as but not limited to the TM^CD4 protein, or biotinylated proteins or antibodies or other molecules reactive with the detection system of choice. It is also obvious that the control lines and other assay parameters could be adjusted to allow detection of any desired level of cells per microlitre, such as the higher levels (around 2,000 cells per microlitre or even higher) that may be useful in monitoring of pediatric samples.

Example 11

Rapid, Point of Care Assay Detection of CD4 T-Cells in Whole Blood

Figure 23:
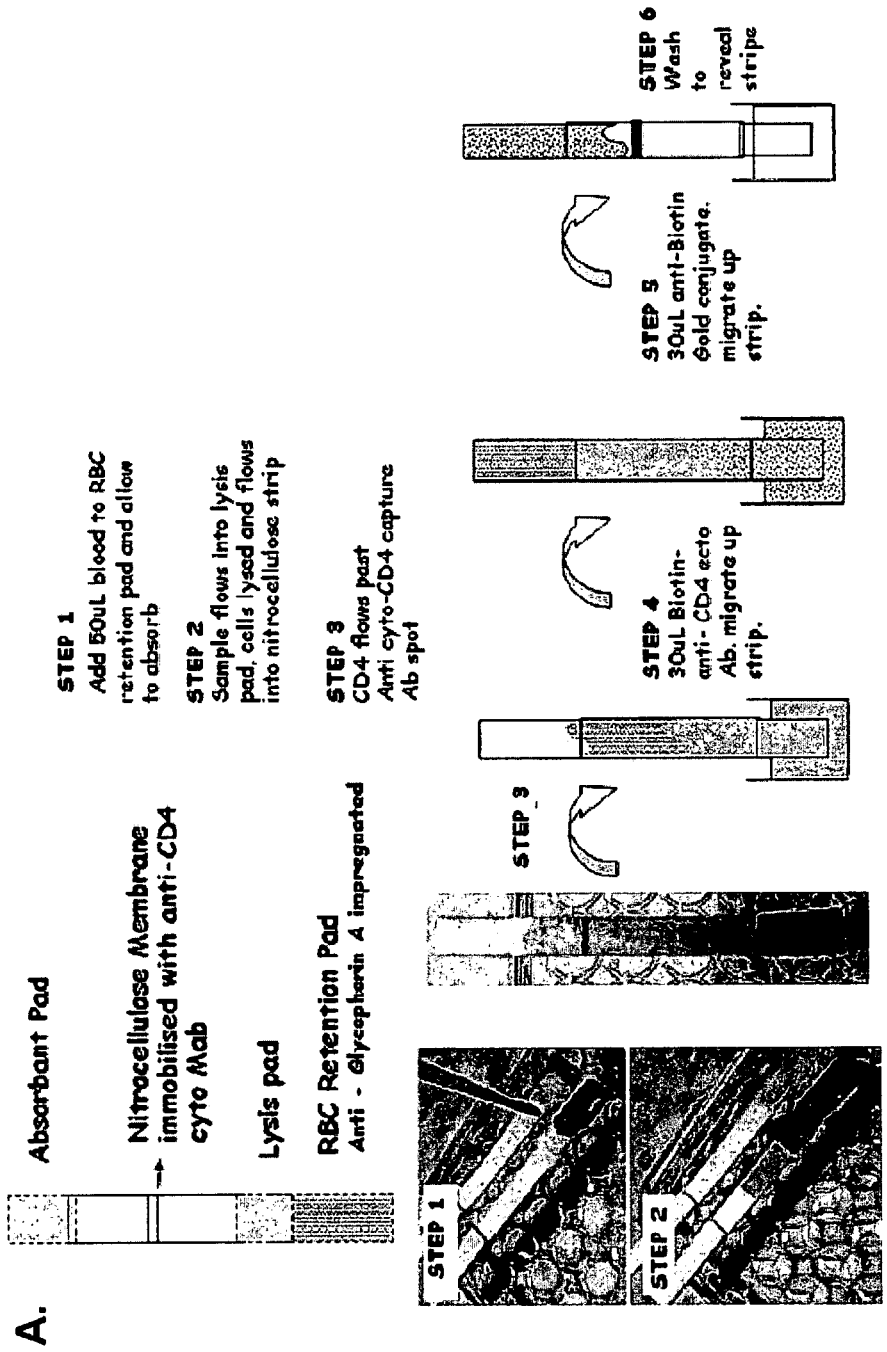
FIG. 23(A) is a schematic representation of a whole-blood CD4 rapid point of care assay in accordance with the present invention. (B). A sample of whole blood containing high CD4 T-cell levels (1452/µl by flow cytometry) was tested in the whole blood assay as shown in A, with detergent in the lysis pad as normal ("+TX"), or with omission of the detergent from the lysis pad ("−TX"). In this example, CD4 signal is only seen in the rapid test when detergent is present to lyse the T-cells in the pad. (C). Examples of representative whole-blood samples assayed in the CD4 rapid point of care assay. CD4 counts for each sample by flow cytometry are shown, and it can be seen that high CD4 T-cell counts give stronger signals while low CD4 T-cell counts give weak signals in this whole blood format.
Figure 23:
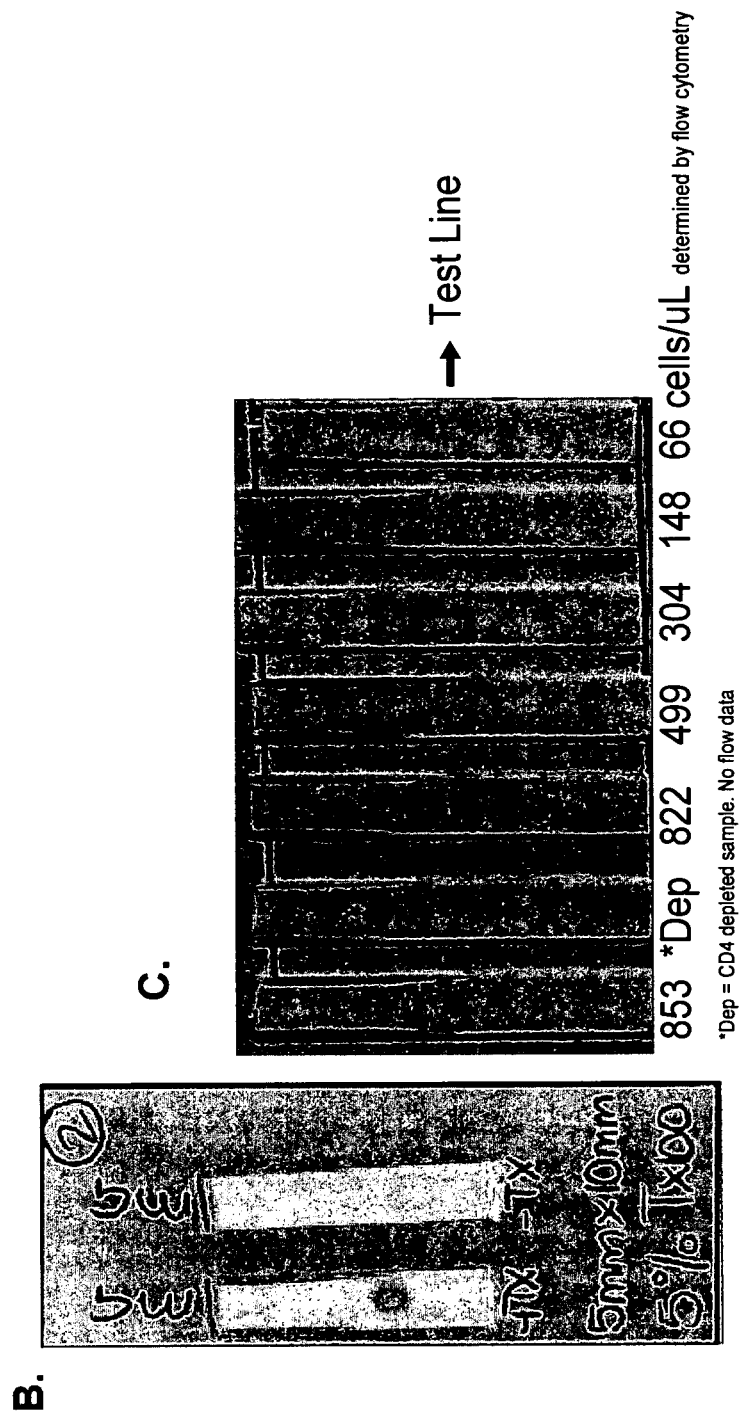

FIG. 23A provides a schematic representation of one embodiment the whole-blood CD4 rapid point of care assay. Red blood cells are captured by anti-glycophorin A (Epiclon anti-N with 0.1% azard Cat No 00992311 (HM1) Commonwealth Serum Laboratories (CSL)) in the RBC retention pad using methods well known in the art, while plasma and white blood cells (including CD4 T-cells) flow into the detergent-impregnated lysis pad, where cells are lysed to release CD4 that can then flow into the test strip to react with the anti-CD4 Cyto Mab for subsequent detection with the biotin anti-CD4 ecto Mab and anti-biotin colloidal gold (see FIG. 23) (B). A sample of whole blood containing high CD4 T-cell levels (1452/µl by flow cytometry) was tested in the whole blood assay as shown in A, with detergent in the lysis pad as normal ("+TX"), or with omission of the detergent from the lysis pad ("−TX"). In some embodiments, CD4 signal is only seen in the rapid test when detergent such as Triton-X100 is present to lyse the T-cells in the pad (see FIG. 23). This depends upon the nature of the anti-CD4 binding agent and agents that are cell membrane permeable together with detection agents that are cell membrane permeable do not require cell lysis. (C). Examples of representative whole-blood samples assayed in the CD4 rapid point of care assay. CD4 counts for each sample by flow cytometry are shown, and it can be seen that high CD4 T-cell counts give stronger signals while low CD4 T-cell counts give weak signals in this whole blood format.

Example 12

Removal of Specific Cell Population (Monocytes) to Prevent Their Detection in Rapid, Point of Care Assays Monocytes also contain CD4, at a quantity of around 10% that found in CD4 T-cells, and the presence of monocytes in a CD4 protein-based assay could in some circumstances lead to false estimates of CD4 T-cells due to the contribution of monocyte CD4. In the ELISA format of the assay, monocytes can be removed from whole blood before assay by use of anti-CD14 magnetic beads and strong magnets designed for this purpose as described above, in methods well known in the art. This method may also be used for pre-treatment of whole blood before point of care assays, but would require sample handling and processing that is preferably avoided for point-of-care testing. No methods have been described for depletion of a particular white blood cell type or other cell type using methods that are compatible with inclusion in a rapid, point of care assay. The inventors have devised a method for efficient removal of monocytes in the sample pad of the rapid point of care test.

Figure 24:
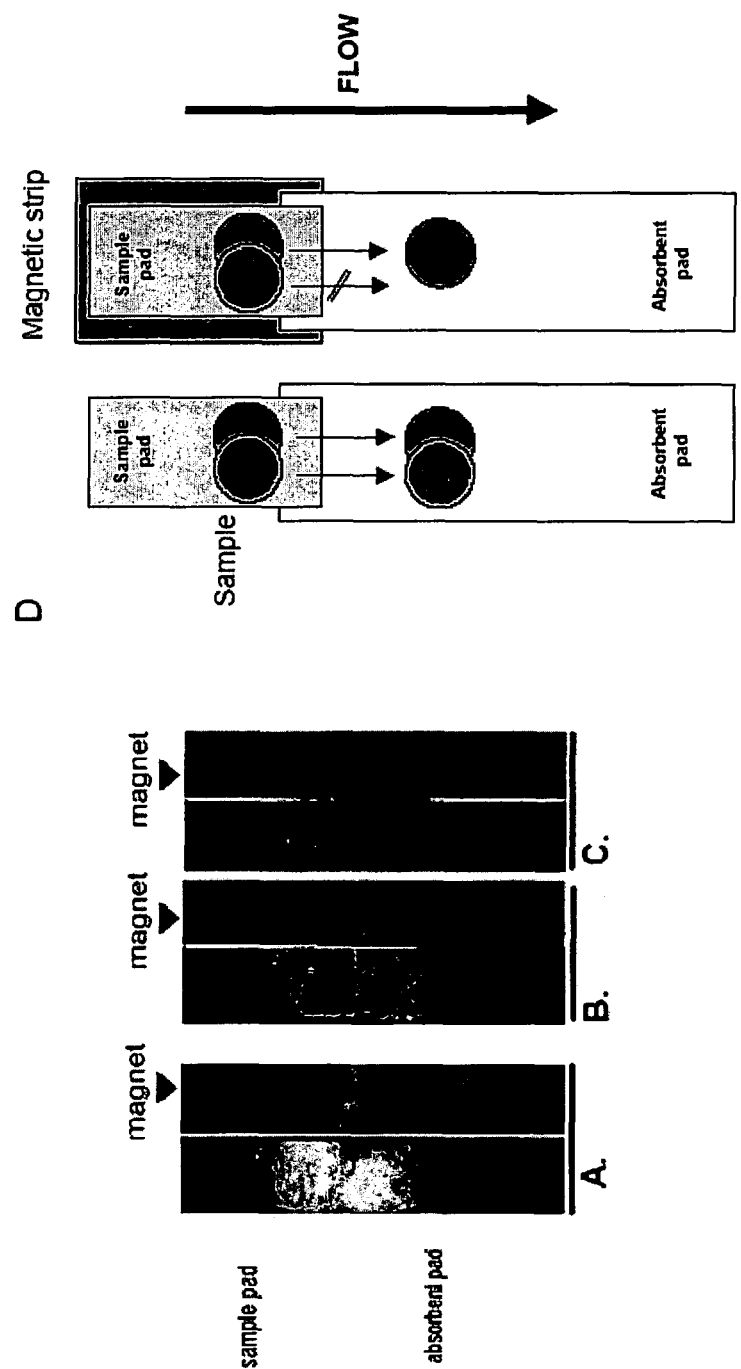
FIG. 24 is a representation of data showing the reduction of monocytes in a sample. In the ELISA format of the assay, monocytes can be removed from whole blood before assay by use of anti-CD14 magnetic beads and strong magnets designed for this purpose as described above, in methods well known in the art. This method may also be used for pre-treatment of whole blood before point of care assays, but would require sample handling and processing that is preferably avoided for point-of-care testing. No methods have been described for depletion of a particular white blood cell type or other cell type using methods that are compatible with inclusion in a rapid, point of care assay. The inventors have devised a method for efficient removal of monocytes in the sample pad of the rapid point of care test as described in Example 12.

This method takes advantage of the surprising observation that by performing the magnetic separation in the thin sample pad (by placement of a magnet above or below the sample pad), the use of a much weaker magnetic field (an inexpensive "fridge magnet") is sufficient to give retention of cells that have reacted with the magnetic beads, rather than an expensive, powerful magnet as used widely in the art when retention is performed in a sample tube. This would allow, for example, the inclusion of a suitable magnet in an inexpensive, single-use disposable device for each individual assay, or an inexpensive multiple-use device or housing for performing multiple assays. In some embodiments, the magnet has a magnetic field of less than about 5 mm such that the field would extend through a sample pad of an immunochromatographic device but not, for example, though all of a suspension of cells in a 1 cm or greater diameter test tube or vessel. One example of a suitable magnet is a ferromagnet which retains its magnetization in the absence of a field. In FIG. 24, purified monocytes and purified peripheral blood leucocytes (PBLs, depleted of monocytes) were separately labelled with infrared fluorescent dyes—monocytes with green (Mini Cell-Vue NIR815, PTI Research, Inc), PBLs with red (Mini Cell-Vue Burgundy, PTI Research Inc.). The images display the same sample pads viewed through different filters on the Licor Odyssey infrared fluorescent scanner: (A)=combined filters, (B)=Em 800, (C)=Em 700. The magnet obscures scanning of the sample pad where it is used. $1.5 \times 10^4$ monocytes (attached to magnetic beads) and $2 \times 10^4$ monocyte depleted PBLs were combined and spotted onto anti-glycophorin A coated sample pads either without (left) or with the magnet (right). Sample was flushed with 60 ul PBS to allow sample to flow into the absorbent pad (used here instead of an actual lysis pad and nitrocellulose test strip for illustrative purposes). Retention of >80% monocytes (green) can be seen in panel (A) and (B) in the presence of a magnet, with no green cells entering the absorbent pad, whilst flow-through of monocyte-depleted PBLs into the absorbent pad is demonstrated in (A) and (C) in both the presence or absence of a magnet. (D) shows a schematic description of the test as shown in (A)-(C). It is obvious to one skilled in the art that a similar method could be used for selective retention or enrichment of any cell population in a filter or sample pad format, prior to the lysis or assay of the desired cells. Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

TABLE 1

Summary of sequence identifiers

| SEQUENCE ID NO: | DESCRIPTION |
|---|---|
| 1 | Peptide 1 of human CD4 cytoplasmic domain |
| 2 | Peptide 2 of human CD4 cytoplasmic domain |
| 3 | Primer 1 for generating construct encoding TM^CD4 |
| 4 | Primer 2 for generating construct encoding TM^CD4 |
| 5 | Primer 3 for generating construct encoding TM^CD4 |
| 6 | Primer 4 for generating construct encoding TM^CD4 |
| 7 | Nucleotide sequence encoding TM^CD4 |
| 8 | Amino acid sequence of TM^CD4 |

TABLE 2

Amino acid sub-classification

| Sub-class | Amino acids |
|---|---|
| Acidic | Aspartic acid, Glutamic acid |
| Basic | Noncyclic: Arginine, Lysine; Cyclic: Histidine |
| Charged | Aspartic acid, Glutamic acid, Arginine, Lysine, Histidine |
| Small | Glycine, Serine, Alanine, Threonine, Proline |
| Polar/neutral | Asparagine, Histidine, Glutamine, Cysteine, Serine, Threonine |
| Polar/large | Asparagine, Glutamine |
| Hydrophobic | Tyrosine, Valine, Isoleucine, Leucine, Methionine, Phenylalanine, Tryptophan |
| Aromatic | Tryptophan, Tyrosine, Phenylalanine |
| Residues that influence chain orientation | Glycine and Proline |

TABLE 3

Exemplary and Preferred Amino Acid Substitutions

| Original Residue | EXEMPLARY SUBSTITUTIONS | PREFERRED SUBSTITUTIONS |
|---|---|---|
| Ala | Val, Leu, Ile | Val |
| Arg | Lys, Gln, Asn | Lys |
| Asn | Gln, His, Lys, Arg | Gln |
| Asp | Glu | Glu |
| Cys | Ser | Ser |
| Gln | Asn, His, Lys, | Asn |
| Glu | Asp, Lys | Asp |
| Gly | Pro | Pro |
| His | Asn, Gln, Lys, Arg | Arg |
| Ile | Leu, Val, Met, Ala, Phe, Norleu | Leu |
| Leu | Norleu, Ile, Val, Met, Ala, Phe | Ile |
| Lys | Arg, Gln, Asn | Arg |
| Met | Leu, Ile, Phe | Leu |
| Phe | Leu, Val, Ile, Ala | Leu |
| Pro | Gly | Gly |
| Ser | Thr | Thr |
| Thr | Ser | Ser |

TABLE 3-continued

Exemplary and Preferred Amino Acid Substitutions

| Original Residue | EXEMPLARY SUBSTITUTIONS | PREFERRED SUBSTITUTIONS |
|---|---|---|
| Trp | Tyr | Tyr |
| Tyr | Trp, Phe, Thr, Ser | Phe |
| Val | Ile, Leu, Met, Phe, Ala, Norleu | Leu |

BIBLIOGRAPHY

Ausubel (Ed) *Current Protocols in Molecular Biology*, 5th Edition, John Wiley & Sons, Inc, NY, 2002.
Bishop et al., *J. Virol. Methods*, 47:203-116. 1994.
Burton et al., *Proc. Natl. Acad. Sci U.S.A.*, 88:10134, 1991.
Chaudhary et al., *Proc. Natl. Acad. Sci. U.S.A.*, 87:1066-1070, 1990.
Clackson et al., *Nature*, 352:624, 1991.
Douillard and Hoffman, Basic Facts about Hybridomas, in *Compendium of Immunology* Vol. II, ed. by Schwartz, 1981.
Glorio-Paulet et al *J Agric Food Chem* 48 (5):1678-1682, 2000.
Janeway et al., *Appendix II. CD Antigens*, Immunology, Garland Publishing, New York, 5th edition, 2001.
Harlow and Lane, *"Antibodies: A Laboratory Manual"* Cold Spring Harbor Laboratory, 1988.
Hoogenboom et al., *Nucleic Acids Res.*, 19:4133, 1991.
Huston et al., *Proc. Natl. Acad. Sci U.S.A.*, 85:5879-5883, 1988.
Kang et al., *Proc. Natl. Acad. Sci. U.S.A.*, 88:4363, 1991;
Kohler and Milstein, *European Journal of Immunology*, 6:511-519, 1976.
Lowman et al., *Biochemistry*, 30:10832, 1991.
Lyamuya et al., J. Imm. Methods, 195:103-112, 1996.
MacGregor et al., *J. Clin. Microbiol.*, 18(5):1237-1243, 1983;
Sambrook, *Molecular Cloning: A Laboratory Manual*, 3rd Edition, CSHLP, CSH, NY, 2001.
Paxton et al., Clin. Diagn. Lab. Immunol., 2(1):104-114, 1995.
Wild D. *"The Immunoassay Handbook"* Nature Publishing Group, 2001.

---

The invention claimed is:

1. A method for evaluating in a blood sample from a subject the number of T-cells bearing CD4, the method comprising:
   (i) contacting the sample with an agent capable of lysing or permeabilizing CD4 T-cells prior to step (ii);
   (ii) contacting the sample with an antibody or antigen-binding fragment thereof that specifically binds to the cytoplasmic domain of CD4 and forms a CD4-antibody complex; and
   (iii) directly or indirectly detecting and evaluating the level or presence of CD4-antibody complex formed in step (ii); and
   wherein the level or presence of the CD4-antibody complex formed in step (ii) comprising the CD4 cytoplasmic domain is indicative of the number of CD4 bearing T-cells in the subject, and wherein the antibody or antigen-binding fragment thereof in step (ii) does not detect soluble CD4 lacking the cytoplasmic domain and thereby, distinguishes between cell-associated CD4 comprising the cytoplasmic domain and soluble CD4 lacking a cytoplasmic domain.

2. The method of claim 1 wherein step (iii) comprises contacting the CD4-antibody complex with a second antibody or antigen-binding fragment thereof that binds to CD4 including binding to the cytoplasmic or extracellular domain and which comprises a detection marker or which is capable of binding to a third binding agent comprising a detection marker, and detecting the detection marker.

3. The method of claim 1 or 2 wherein the method is an Enzyme Linked Immunosorbent Assay (ELISA)-type, flow cytometry or chromatographic method.

4. The method of claim 3, wherein the method is an ELISA-type or chromatographic method and the antibody or antigen-binding fragment thereof that specifically binds to the cytoplasmic domain of CD4 is immobilised on a support.

5. The method of claim 1, wherein in step (ii), the sample is contacted with the antibody or antigen-binding fragment of step (ii) by applying the sample to a sample portion of an immunochromatographic device wherein the device sample portion is operably connected to a capture portion of the device and wherein components of the sample flow from the device sample portion to and through the device capture portion which comprises the antibody or antigen-binding fragment thereof that specifically binds to the cytoplasmic domain of CD4 such that only CD4 comprising the cytoplasmic domain and not soluble CD4 that does not comprise a cytoplasmic domain is captured by the antibody or fragment to form a CD4-antibody complex; and wherein in step (iii), the level or presence of CD4-antibody complex is detected and evaluated by contacting the device capture portion with a second binding agent that binds to CD4 including binding to the cytoplasmic or extracellular domain and which comprises a detection marker or which is capable of binding to a third or subsequent binding agent comprising a detection marker; and detecting the presence of the detection marker.

6. The method of claim 5, further comprising contacting the second binding agent with a third or subsequent binding agent comprising a detection marker.

7. The method of claim 1 or 5 wherein the level or presence of the CD4-antibody complex is compared with a predetermined control wherein the predetermined control is a predetermined amount of a control polypeptide sufficient to produce, when bound to a visual detection marker, a signal providing an internal visual reference equivalent to the signal produced by a predetermined number of CD4 T-cells.

8. The method of claim 7 wherein the control polypeptide is CD4 polypeptide comprising the cytoplasmic domain of CD4.

9. The method of claim 1 wherein the number of CD4-bearing T-cells is one or more of less than 200, less than 250, more than 250, 250 to 350, 350 to 500, 250 to 500 and more than 500 cells/µl of blood.

10. The method of claim 1 wherein the number of CD4 T-cells is one or more of less than 200, less than 500, 500 to 1,000, 1,000 to 2,000, and more than 2,000 cells/µl of blood.

11. The method of claim 1 further comprising depleting monocytes in the sample by contacting the sample with anti-CD14 antibodies bound to a support.

12. The method of claim 1 further comprising depleting red blood cells in the sample by contacting the sample with anti-glycophorin antibodies bound to a support.

* * * * *

UNITED STATES PATENT AND TRADEMARK OFFICE
CERTIFICATE OF CORRECTION

PATENT NO.        : 8,409,818 B2
APPLICATION NO.   : 12/443306
DATED             : April 2, 2013
INVENTOR(S)       : David Andrew Anderson et al.

It is certified that error appears in the above-identified patent and that said Letters Patent is hereby corrected as shown below:

In the Specification

It should read:
(Column 1, Line 51) occurs *via* receptors or cell surface associated molecules It should read:
(Column 3, Line 57) mutatis *mutandis* to every other embodiment unless expressly It should read:
(Column 7, Line 39) of $CD4^+$ T-cells *per* microlitre It should read:
(Column 7, Line 44) between OD450-620 and the number of $CD4^+$ T-cells *per*

It should read:
(Column 9, Line 41) with the magnet (right). Sample was flushed with 60µl PBS It should read:
(Column 12, Line 34) markers are used to tag CSAP and a high $T_c$ superconducting It should read:
(Column 12, Line 41) formats of ELISA are disclosed in the art and are known to It should read:
(Column 13, Line 29) bound to other portions of the device *via* antibodies to the It should read:
(Column 14, Line 15) from the sample portion to and through the capture portion Signed and Sealed this
Twenty-second Day of April, 2014

Michelle K. Lee
*Deputy Director of the United States Patent and Trademark Office*

It should read:
(Column 14, Line 64) mats are available. However, in one embodiment a method for It should read:
(Column 15, Line 6) to and through the capture portion which comprises an anti- It should read:
(Column 15, Line 33) the sample with anti-CD14 antibodies bound to a solid or It should read:
(Column 17, Line 46) CSAP bearing cells will flow over the capture portion towards It should read:
(Column 19, Line 31) CD97, CD98, CD100, CD101, CD102, CD103, It should read:
(Column 22, Line 10) nized donors. Antibodies comprising scFvs from any species It should read:
(Column 25, Line 36) conjugated to anti-CD4 antibody and an absorbent material It should read:
(Column 29, Lines 51-52) Vue Burgundy, PTI Research Inc.). The images display the It should read:
(Column 29, Line 60) (right). Sample was flushed with 60µl PBS to allow sample to It should read:
(Column 30, Line 5) prior to the lysis or assay of the desired cells.
            Those skilled in It should read:
(Column 30, Line 33) Sub-classes It should read:
(Column 31, Line 15) Bishop et al., *J. Virol. Methods*, 47:203-216. 1994.

In the Claims

It should read:
(Column 38, Line 43)(claim 7) mined control, wherein the predetermined control is a prede-

SEQUENCE LISTING

<160> NUMBER OF SEQ ID NOS: 8

<210> SEQ ID NO 1
<211> LENGTH: 17
<212> TYPE: PRT
<213> ORGANISM: homo sapien

<400> SEQUENCE: 1

Lys Arg Leu Leu Ser Glu Lys Lys Thr Cys Pro His Arg Phe Gln Lys
1               5                   10                  15

Thr

<210> SEQ ID NO 2
<211> LENGTH: 20
<212> TYPE: PRT
<213> ORGANISM: homo sapien

<400> SEQUENCE: 2

Cys Arg His Arg Arg Arg Gln Ala Glu Arg Met Ser Gln Ile Lys Arg
1               5                   10                  15

Leu Leu Ser Glu
            20

<210> SEQ ID NO 3
<211> LENGTH: 29
<212> TYPE: DNA
<213> ORGANISM: Artificial Sequence
<220> FEATURE:
<223> OTHER INFORMATION: Synthetic oligonucleotide primer

<400> SEQUENCE: 3
cgggaattca caatgaaccg gggagtccc                                           29

<210> SEQ ID NO 4
<211> LENGTH: 31
<212> TYPE: DNA
<213> ORGANISM: Artificial Sequence
<220> FEATURE:
<223> OTHER INFORMATION: Synthetic oligonucleotide primer

<400> SEQUENCE: 4

```
ggctctagat caaatggggc tacatgtctt c                              31
```

<210> SEQ ID NO 5
<211> LENGTH: 36
<212> TYPE: DNA
<213> ORGANISM: Artificial Sequence
<220> FEATURE:
<223> OTHER INFORMATION: Synthetic oligonucleotide primer

<400> SEQUENCE: 5

```
gccttcggtg ccggcacctc tgcaccgggg tggacc                         36
```

<210> SEQ ID NO 6
<211> LENGTH: 36
<212> TYPE: DNA
<213> ORGANISM: Artificial Sequence
<220> FEATURE:
<223> OTHER INFORMATION: Synthetic oligonucleotide primer

<400> SEQUENCE: 6

```
ggtccacccc ggtgcagagg tgccggcacc gaaggc                         36
```

<210> SEQ ID NO 7
<211> LENGTH: 1425
<212> TYPE: DNA
<213> ORGANISM: Artificial Sequence
<220> FEATURE:
<223> OTHER INFORMATION: Nucleotide sequence encoding TMCD4

<400> SEQUENCE: 7

```
atgggggtt ctcatcatca tcatcatcat ggtatggcta gcatgactgg tggacagcaa    60
atgggtcggg atctgtacga cgatgacgat aaggtaccag atccagtgt ggtggaattc   120
acaatgaacc ggggagtccc ttttaggcac ttgcttctgg tgctgcaact ggcgctcctc   180
ccagcagcca ctcagggaaa gaaagtggtg ctgggcaaaa agggggatac agtggaactg   240
acctgtacag cttcccagaa gaagagcata caattccact ggaaaaactc caaccagata   300
aagattctgg gaaatcaggg ctccttctta actaaaggtc catccaagct gaatgatcgc   360
gctgactcaa gaagaagcct tgggaccaa ggaaactttc ccctgatcat caagaatctt   420
aagatagaag actcagatac ttacatctgt gaagtggagg accagaagga ggaggtgcaa   480
ttgctagtgt tcggattgac tgccaactct gacacccacc tgcttcaggg gcagagcctg   540
acctgacct ggagagccc cctggtagt agcccctcag tgcaatgtag agtccaagg   600
ggtaaaaaca tagaggggg gaagaccctc tccgtgtctc agctggagct ccaggatagt   660
ggcacctgga catgcactgt cttgcagaac cagaagaagg tggagttcaa aatagacatc   720
gtggtgctag ctttccagaa ggcctccagc atagtctata agaagaggg ggaacaggtg   780
gagttctcct tcccactcgc ctttacagtt gaaaagctga cggcagtgg cgagctgtgg   840
tggcaggcgg agagggcttc ctcctccaag tcttggatca cctttgacct gaagaacaag   900
gaagtgtctg taaaacgggt tacccaggac cctaagctcc agatgggcaa gaagctcccg   960
ctccacctca ccctgcccca ggccttgcct cagtatgctg gctctggaaa cctcaccctg  1020
gcccttgaag cgaaaacagg aaagttgcat caggaagtga acctggtggt gatgagagcc  1080
actcagctcc agaaaatttt gacctgtgag gtgtgggac ccacctcccc taagctgatg  1140
ctgagtttga aactggagaa caaggaggca aaggtctcga agcgggagaa ggcggtgtgg  1200
gtgctgaacc ctgaggcggg gatgtggcag tgtctgctga gtgactcggg acaggtcctg  1260
ctggaatcca acatcaaggt tctgcccaca tggtccaccc cggtgcagag gtgccggcac  1320
```

```
cgaaggcgcc aagcagagcg gatgtctcag atcaagagac tcctcagtga gaagaagacc    1380
tgccagtgtc ctcaccggtt tcagaagaca tgtagcccca tttga                    1425
```

<210> SEQ ID NO 8
<211> LENGTH: 472
<212> TYPE: PRT
<213> ORGANISM: Artificial Sequence
<220> FEATURE:
<223> OTHER INFORMATION: Amino acid sequence of TMCD4

<400> SEQUENCE: 8

```
Met Gly Gly Ser His His His His His Gly Met Ala Ser Met Thr
1               5                   10                  15

Gly Gly Gln Gln Met Gly Arg Asp Leu Tyr Asp Asp Asp Lys Val
            20                  25                  30

Pro Gly Ser Ser Val Val Glu Phe Thr Met Asn Arg Gly Val Pro Phe
            35                  40                  45

Arg His Leu Leu Leu Val Leu Gln Leu Ala Leu Leu Pro Ala Ala Thr
50                  55                  60

Gln Gly Lys Lys Val Val Leu Gly Lys Lys Gly Asp Thr Val Glu Leu
65                  70                  75                  80

Thr Cys Thr Ala Ser Gln Lys Lys Ser Ile Gln Phe His Trp Lys Asn
                85                  90                  95

Ser Asn Gln Ile Lys Ile Leu Gly Asn Gln Gly Ser Phe Leu Thr Lys
                100                 105                 110

Gly Pro Ser Lys Leu Asn Asp Arg Ala Asp Ser Arg Arg Ser Leu Trp
            115                 120                 125

Asp Gln Gly Asn Phe Pro Leu Ile Ile Lys Asn Leu Lys Ile Glu Asp
130                 135                 140

Ser Asp Thr Tyr Ile Cys Glu Val Glu Asp Gln Lys Glu Glu Val Gln
145                 150                 155                 160

Leu Leu Val Phe Gly Leu Thr Ala Asn Ser Asp Thr His Leu Leu Gln
                165                 170                 175

Gly Gln Ser Leu Thr Leu Thr Leu Glu Ser Pro Pro Gly Ser Ser Pro
            180                 185                 190

Ser Val Gln Cys Arg Ser Pro Arg Gly Lys Asn Ile Gln Gly Gly Lys
            195                 200                 205

Thr Leu Ser Val Ser Gln Leu Glu Leu Gln Asp Ser Gly Thr Trp Thr
210                 215                 220

Cys Thr Val Leu Gln Asn Gln Lys Lys Val Glu Phe Lys Ile Asp Ile
225                 230                 235                 240

Val Val Leu Ala Phe Gln Lys Ala Ser Ser Ile Val Tyr Lys Lys Glu
                245                 250                 255

Gly Glu Gln Val Glu Phe Ser Phe Pro Leu Ala Phe Thr Val Glu Lys
            260                 265                 270

Leu Thr Gly Ser Gly Glu Leu Trp Trp Gln Ala Glu Arg Ala Ser Ser
            275                 280                 285

Ser Lys Ser Trp Ile Thr Phe Asp Leu Lys Asn Lys Glu Val Ser Val
    290                 295                 300

Lys Arg Val Thr Gln Asp Pro Lys Leu Gln Met Gly Lys Lys Leu Pro
305                 310                 315                 320

Leu His Leu Thr Leu Pro Gln Ala Leu Pro Gln Tyr Ala Gly Ser Gly
                325                 330                 335

Asn Leu Thr Leu Ala Leu Glu Ala Lys Thr Gly Lys Leu His Gln Glu
            340                 345                 350
```

-continued

```
Val Asn Leu Val Val Met Arg Ala Thr Gln Leu Gln Lys Asn Leu Thr
    355                 360                 365

Cys Glu Val Trp Gly Pro Thr Ser Pro Lys Leu Met Leu Ser Leu Lys
    370                 375                 380

Leu Glu Asn Lys Glu Ala Lys Val Ser Lys Arg Glu Lys Ala Val Trp
385                 390                 395                 400

Val Leu Asn Pro Glu Ala Gly Met Trp Gln Cys Leu Leu Ser Asp Ser
                405                 410                 415

Gly Gln Val Leu Leu Glu Ser Asn Ile Lys Val Leu Pro Thr Trp Ser
            420                 425                 430

Thr Pro Val Gln Arg His Arg Arg Gln Ala Glu Arg Met Ser Gln
        435                 440                 445

Ile Lys Arg Leu Leu Ser Glu Lys Lys Thr Cys Gln Cys Pro His Arg
        450                 455                 460

Phe Gln Lys Thr Cys Ser Pro Ile
465                 470
```